United States Patent
Dong et al.

(10) Patent No.: US 9,550,986 B2
(45) Date of Patent: Jan. 24, 2017

(54) HIGH-THROUGHPUT ANTIBODY HUMANIZATION

(71) Applicant: AbbVie, Inc., North Chicago, IL (US)

(72) Inventors: Feng Dong, Lansdale, PA (US); Lorenzo Benatuil, Northborough, MA (US); Jijie Gu, Shrewsbury, MA (US); Chung-Ming Hsieh, Newton, MA (US)

(73) Assignee: AbbVie Inc., North Chicago, IL (US)

( * ) Notice: Subject to any disclaimer, the term of this patent is extended or adjusted under 35 U.S.C. 154(b) by 212 days.

(21) Appl. No.: 14/136,076

(22) Filed: Dec. 20, 2013

(65) Prior Publication Data

US 2014/0213770 A1    Jul. 31, 2014

Related U.S. Application Data

(60) Provisional application No. 61/740,900, filed on Dec. 21, 2012, provisional application No. 61/783,999, filed on Mar. 14, 2013.

(51) Int. Cl.
*C12P 21/04* (2006.01)
*C12N 15/10* (2006.01)
*C40B 30/02* (2006.01)
*C07K 16/46* (2006.01)

(52) U.S. Cl.
CPC ......... *C12N 15/1089* (2013.01); *C07K 16/465* (2013.01); *C40B 30/02* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,223,409 A | 6/1993 | Ladner et al. |
| 5,225,539 A | 7/1993 | Winter |
| 5,258,498 A | 11/1993 | Huston et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,648,260 A | 7/1997 | Winter et al. |
| 5,658,727 A | 8/1997 | Barbas et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits |
| 5,723,323 A | 3/1998 | Kauffman |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,780,225 A | 7/1998 | Wigler et al. |
| 5,814,476 A | 9/1998 | Kauffman |
| 5,817,483 A | 10/1998 | Kauffman |
| 5,821,047 A | 10/1998 | Garrard et al. |
| 5,824,514 A | 10/1998 | Kauffman |
| 5,969,108 A | 10/1999 | McCafferty et al. |
| 5,976,862 A | 11/1999 | Kauffman et al. |
| 6,180,370 B1 | 1/2001 | Queen et al. |
| 6,204,023 B1 | 3/2001 | Robinson et al. |
| 6,350,861 B1 | 2/2002 | Co et al. |
| 6,699,658 B1 | 3/2004 | Wittrup et al. |
| 8,398,966 B2 * | 3/2013 | Wu .......................... C12N 9/96 424/85.2 |
| 2002/0137134 A1 | 9/2002 | Gerngross |
| 2003/0186374 A1 | 10/2003 | Hufton |
| 2004/0018590 A1 | 1/2004 | Gerngross |
| 2011/0142761 A1 * | 6/2011 | Wu .......................... C12N 9/96 424/9.1 |

FOREIGN PATENT DOCUMENTS

| | | |
|---|---|---|
| EP | 0239400 B1 | 3/1987 |
| EP | 0592106 A1 | 4/1994 |
| EP | 1176195 A1 | 1/2002 |
| EP | 0519596 B1 | 2/2005 |
| WO | WO9002809 A1 | 3/1990 |
| WO | WO9005144 A1 | 5/1990 |
| WO | WO9014424 A1 | 11/1990 |
| WO | WO9014430 A1 | 11/1990 |
| WO | WO9014443 A1 | 11/1990 |
| WO | WO9109967 A1 | 7/1991 |

(Continued)

OTHER PUBLICATIONS

Hwang et al., "Use of human germline genes in a CDR homology-based approach to antibody humaniziation", Methods, 2005: vol. 36: pp. 35-42.*
U.S. Appl. No. 14/141,502, filed Dec. 27, 2013, Tariq Ghayur.
U.S. Appl. No. 14/106,116, filed Dec. 13, 2013, Jane Seagal.
PCT/US13/74941, filed Dec. 13, 2013, Jane Seagal.
U.S. Appl. No. 14/141,498, filed Dec. 27, 2013, Lorenzo Benatuil.
PCT/US13/77912, filed Dec. 27, 2013, Lorenzo Benatuil.
U.S. Appl. No. 14/141,500, filed Dec. 27, 2013, Lorenzo Benatuil.
U.S. Appl. No. 14/141,501, filed Dec. 27, 2013, Jijie Gu.
PCT/US13/77933, filed Dec. 27, 2013, Jijie Gu.

(Continued)

*Primary Examiner* — Michael Burkhart

(74) *Attorney, Agent, or Firm* — Lathrop & Gage LLP; James H. Velema, Esq.

(57) ABSTRACT

The present invention relates to improved methods for antibody engineering, e.g., humanization. In particular, the disclosure provides a high-throughput antibody humanization process that can be automated by computer-implementation.

14 Claims, 11 Drawing Sheets

(56) References Cited

FOREIGN PATENT DOCUMENTS

| WO | WO9110737 A1 | 7/1991 |
|---|---|---|
| WO | WO9117271 A1 | 11/1991 |
| WO | WO9201047 A1 | 1/1992 |
| WO | WO9202551 A1 | 2/1992 |
| WO | WO9203461 A1 | 3/1992 |
| WO | WO9209690 A2 | 6/1992 |
| WO | WO9211272 A1 | 7/1992 |
| WO | WO9215679 A1 | 9/1992 |
| WO | WO9218619 A1 | 10/1992 |
| WO | WO9220791 A1 | 11/1992 |
| WO | WO9222324 A1 | 12/1992 |
| WO | WO9301288 A1 | 1/1993 |
| WO | WO9306213 A1 | 4/1993 |
| WO | WO9311236 A1 | 6/1993 |
| WO | WO9418219 A1 | 8/1994 |
| WO | WO9515982 A2 | 6/1995 |
| WO | WO9520401 A1 | 8/1995 |
| WO | WO9720032 A1 | 6/1997 |
| WO | WO9729131 A1 | 8/1997 |
| WO | WO9831700 A1 | 7/1998 |
| WO | WO9906834 A2 | 2/1999 |
| WO | WO9954342 A1 | 10/1999 |
| WO | WO0037504 A2 | 6/2000 |
| WO | WO0056772 A1 | 9/2000 |
| WO | WO03016466 A2 | 2/2003 |
| WO | WO03035835 A2 | 5/2003 |
| WO | WO2005007699 A2 | 1/2005 |
| WO | WO2005100584 A2 | 10/2005 |
| WO | WO2007014162 A2 | 2/2007 |
| WO | 2010/006059 A1 | 1/2010 |
| WO | 2011/047266 A1 | 4/2011 |
| WO | 2012/024187 A1 | 2/2012 |

OTHER PUBLICATIONS

U.S. Appl. No. 14/136,076, filed Dec. 20, 2013, Feng Dong.
PCT/US13/76817, filed Dec. 20, 2013, Feng Dong.
U.S. Appl. No. 14/097,033, filed Dec. 4, 2013, Denise Karaoglu Hanzatian.
PCT/US13/73114, filed Dec. 4, 2013, Denise Karaoglu Hanzatian.
U.S. Appl. No. 14/141,503, filed Dec. 27, 2013, Tariq Ghayur.
U.S. Appl. No. 14/141,504, filed Dec. 27, 2013, Tariq Ghayur.
U.S. Appl. No. 14/141,499, filed Dec. 27, 2013, Tariq Ghayur.
PCT/US13/77908, filed Dec. 27, 2013, Tariq Ghayur.
Ames et al., 'Conversion off Murine Fabs Isolated From a Cominatorial Phage Display Library to Full Length Immunoglobulins'. 1995 Journal of Immunological Methods vol. 184 pp. 177-186.
Azzazy et al., 'Phage Display Technology: Clinical Applications and Recent Innovations'. 2002 Clinical Biochemistry vol. 35 pp. 425-445.
Babcook et al., 'A Novel Strategy for Generating Monoclonal Antibodies From Single, Isolated Lymphocytes Producing Antibodies of Defined Specificities'. 1996 Immunology vol. 93 pp. 7843-7848.
Barbas et al., 'Assembly of Combinatorial Antibody Libraries on Phage Surfaces: The Gene III Site'. 1991 Biochemistry vol. 88 pp. 7978-7982.
Better et al., '*Escherichia coli* Secretion of an Active Chimeric Antibody Fragment'. 1988 Science vol. 240 pp. 1041-1043.
Bird et al., 'Single-Chain Antigen-Binding Proteins'. 1988 Science vol. 242 pp. 423-426.
Brinkmann et al., 'Phage Display of Disulfide-Stabilized Fv Fragments'. 1995 Journal of Immunological Methods vol. 182 pp. 41-50.
Burton et al., 'Human Antibodies from Combinatorial Libraries'. 1994 Advances in Immunology vol. 57 pp. 190-280.
Carter et al., 'Humanization of an Anti-p185HER2 Antibody for Human Cancer Therapy'. 1992 Immunology vol. 89 pp. 4285-4289.

Chothia and Lesk, 'Canonical Structures for the Hypervariable Regions of Immunoglobulins'. 1987 Journal of Molecular Biology vol. 196 pp. 901-917.
Chothia et al., 'Conformations of Immunoglobulin Hypervariable Regions'. 1989 Nature vol. 342 pp. 877-883.
Chothia et al., 'Structural Repertoire of the Human Vh Segments'. 1992 Journal of Molecular Biology vol. 227 pp. 799-817.
Clackson et al., 'Making Antibody Fragments Using Phage Display Libraries'. 1991 Nature vol. 352 pp. 624-628.
Foote et al., 'Antibody Framework Residues Affecting the Conformation of the Hypervariable Loops'. 1992 Journal of Molecular Biology vol. 224 pp. 487-499.
Fuchs et al., 'Targeting Recombinant Antibodies to the Surface of *Escherichia coli*: Fusion to a Peptidoglycan Associated Lipoprotein'. 1991 Biotechnology vol. 9 pp. 1369-1372.
Garrard et al., 'Fab Assembly and Enrichment in a Monovalent Phage Display System'. 1991 Biotechnology vol. 9 pp. 1373-1377.
Gavilondo et al., 'Antibody Engineering At the Millenium'. 2000 BioTechniques vol. 29 pp. 128-145.
Giege et al., 'An Introduction to the Crystallogensis of Biological Macromolecules'. 1999.
Gram et al., 'In Vitro Selection and Affinity Maturation of Antibodies from a Naive Combinatorial Immunoglobulin Library'. 1992 Biochemistry vol. 89 pp. 3576-3580.
Griffiths et al., 'Human Anti-self Antibodies with High Specificity From Phage Display Libraries'. 1993 vol. 12 No. 2 pp. 725-723.
Hammerling et al., 'Production of Antibody-Producing Hybridomas in the Rodent Systems'. 1981 Research Monographs in Immunology vol. 3 pp. 563-587.
Hawkins et al., 'Selection of Phage Antibodies by Binding Affinity Mimicking Affinity Maturation'. 1992 Journal of Molecular Biology vol. 226 No. 3 pp. 889-896.
Hay et al., 'Bacteriophage Cloning and *Escherichia coli* Expression of a Human IgM Fab'. 1992 Human Antibody Hybridomas vol. 3 pp. 81-85.
Holliger et al., '"Diabodies": Small Bivalent and Bispecific Antibody Fragments'. 1993 Biophysics vol. 90 pp. 6444-6448.
Hoogenboom et al., 'Designing and Optimizing Library Selection Strategies for Generating High-Affinity Anitbodies'. 1997 Trends in Biotechnology vol. 15 pp. 62-70.
Hoogenboom et al., 'Multi-Subunit Proteins on the Surface of Filamentous Phage: Methodologies for Displaying Antibody (Fab) Heavy and Light Chains'. 1991 Nucleic Acids Research vol. 19 No. 15 pp. 4133-4137.
Hoogenboom et al., 'Natural and Designer Binding Sites Made by Phage Display Technology'. 2000 Immunology Today vol. 21 No. 8 pp. 371-378.
Huse et al., 'Generation of a Large Combinatorial Library of the Immunological Repertoire in Phage Lambda'. 1989 Science vol. 246 pp. 1275-1281.
Huston et al., 'Protein Engineering of Antibody Binding Sites: Recovery of Specific Activity in an Anti-digoxin Single-Chain Fv Analogue Produced in *Escherichia coli*'. 1988 Biochemistry vol. 85 pp. 5879-5883.
Huston et al., 'Protein Engineering of Single-Chain Fv Analogs and Fusion Proteins'. 1991 Antibodies and Antigens vol. 203 pp. 46-88.
Johnsson et al., 'Immobilization of Proteins to a Carboxymethyldextran-Modified Gold Surface for a Biospecific Interaction Analysis in Surface Plasmon Resonance Sensors'. 1991 Analytical Biochemistry vol. 198 pp. 268-277.
Johnsson et al., 'Comparison of Methods of Immobilization to a Carboxymethyl Dextran Sensor Surfaces by Analysis of the Specific Activity of Monoclonal Antibodies'. 1995 Journal of Molecular Recognition vol. 8 pp. 125-131.
Jones et al., 'Replacing the Complementarity-Determining Regions in a Human Anitbody With Those From a Mouse'. 1986 Nature vol. 321 pp. 522-525.
Jonsson et al., 'Real-Time Biospecific Interaction Analysis Using Surface Plasmon Resonance and a Sensor Chip Technology'. 1991 Biotechniques vol. 11 No. 5 pp. 620-627.
Jonsson et al., 'Introducing a Biosensor Based Technology for Real-Time Biospecific Interaction Analysis'. 1993 Annales De Biologie Clinque vol. 51 pp. 19-26.

(56) References Cited

OTHER PUBLICATIONS

Kabat et al., 'Attempts to Locate Complementarity-Determining Residues in the Variable Positions of Light and Heavy Chains'. 1971 Annals New York Academy of Sciences pp. 382-393.
Kaufman and Sharp, 'Amplification and Expression of Sequences Cotransfected with a Modular Dihydrofolate Reductase Complementary DNA Gene'. 1982 Journal of Molecular Biology vol. 159 pp. 601-621.
Kellermann et al., 'Antibody Discovery: the Use of Transgenic Mice to Generate Human Monoclonal Anitbodies for Therapeutics'. 2002 Pharmaceutical Biotechnology pp. 593-597.
Kettleborough et al., 'Isolation of Tumor Cell-Specific Single-Chain Fv From Immunized Mice Using Phage-Antibody Libraries and the Reconstruction of Whole Antibodies from these Antibody Fragments'. 1994 European Journal of Immunology vol. 24 pp. 952-958.
Kipriyanov et al., 'Recombinant Single-Chain Fv Fragments Carrying C-Terminal Cysteine Residues: Production of Bivalent and Biotinylated Miniantibodies'. 1994 Molecular Immunology vol. 31 No. 14 pp. 1047-1058.
Kipriyanov et al., 'Single-Chain Antibody Streptavidin Fusions: Tetrameric Bifunctional scFv-Complexes with Biotin Binding Activity and Enhanced Affinity to Antigen'. 1995 Human Antibody Hybridomas vol. 6 No. 3 pp. 93-101.
Little et al., 'Of Mice and Men: Hybridomas and Recombinant Antibodies'. 2000 Immunology Today vol. 21 No. 8 pp. 364-370.
MacCallum et al., 'Antibody-Antigen Interactions: Contact Analysis and Binding Site Topography'. 1996 Journal of Molecular Biology vol. 262 pp. 732-745.
Marchalonis et al., 'Evolutionary Factors in the Emergence of the Combinatorial Germline Antibody Repertoire'. 2001 Advances in Experimental Medicine and Biology vol. 484 pp. 13-30.
McCafferty et al., 'Phage Antibodies: Filamentous Phage Displaying Antibody Variable Domains'. 1990 Nature vol. 348 pp. 552-554.
Mullinax et al., 'Expression of a Heterodimeric Fab Antibody Protein in One Cloning Step'. 1992 BioTechniques vol. 12 No. 6 pp. 864-869.
Padlan et al., 'A Possible Procedure for Reducing the Immunogenicity of Antibody Variable Domains While Preserving Their Ligand-Binding Properties'. 1991 Molecular Immunology vol. 28 No. 4-5 pp. 489-498.
Padlan et al., 'Identification of Specificity-Determining Residues in Antibodies'. 1995 The FASEB Journal vol. 9 pp. 133-139.
Persic et al., 'An Integrated Vector System for the Eukaryotic Expression of Antibodies or their Fragments After Selection from Phage Display Libraries'. 1997 Gene vol. 187 pp. 9-18.
Poljak et al., 'Production and Structure of Diabodies'. 1994 Structure vol. 2 No. 12 pp. 1121-1123.

International Search Report with Written Opinion corresponding to International Patent Application No. PCT/US2013/076817, mailed May 30, 2014.
Presta et al., 'Humanization of an Antibody Against IgE'. 1993 The Journal of Immunology vol. 151 No. 5 pp. 2623-2632.
Riechmann et al., 'Reshaping Human Antibodies for Therapy'. 1988 Nature vol. 332 pp. 322-327.
Roberts et al., 'RNA-peptide Fusions for the In Vitro Selection of Peptides and Proteins'. 1997 Biochemistry vol. 94 pp. 12297-12302.
Roguska et al., 'Humanization of Murine Monoclonal Antibodies through Variable Domain Resurfacing'. 1994 Biochemistry vol. 91 pp. 969-973.
Sawai et al., 'Direct Production of the Fab Fragment Derived From the Sperm Immobilizing Antibody Using Polymerase Chain Reaction and cDNA Expression Vectors'. 1995 American Journal of Reproductive Immunology vol. 34 pp. 26-34.
Shapiro et al., 'DNA Targets Motifs of Somatic Mutagenesis in Antibody Genes' 2002 Critical Reviews in Immunology vol. 22 No. 3 pp. 183-200.
Shields et al., 'Lack of Fucose on Human IgG1 N-Linked Oligosaccharide Improves Binding to Human Fc(?)RIII and Antibody-Dependent Cellular Toxicity'. 2002 The Journal of Biological Chemistry vol. 277 No. 30 pp. 26733-26740.
Shu et al., 'Secretion of a Single-Gene-Encoded Immunoglobulin from Myeloma Cells'. 1993 Immunology vol. 90 pp. 7995-7999.
Sims et al., 'A Humanized CD18 Antibody Can Block Function without Cell Destruction'. 1993 The Journal of Immunology vol. 151 No. 4 pp. 2296-2308.
Skerra et al., 'Assembly of a Functional Immunoglobulin Fv Fragment in *Escherichia coli*'. 1988 Science vol. 240 pp. 1038-1041.
Studnicka et al., 'Human-Engineered Monoclonal Antibodies Retain Full Specific Binding Activity by Preserving non-CDR Complementarity-Modulating Residues'. 1994 Protein Engineering vol. 7 No. 6 pp. 805-814.
Taylor et al., 'A Transgenic Mouse that Expresses a Diversity of Human Sequence Heavy and Light Chain Immunoglobulins'. 1992 Nucleic Acids Research vol. 20 No. 23 pp. 6287-6295.
Umana et al., 'Engineered Glycoforms of an Antineuro-blastoma IgG1 with Optimized Antibody-dependent Cellular Cytotoxic Activity'. 1999 Nature Biotechnology vol. 17 pp. 176-180.
Urlaub et al., 'Isolation of Chinese Hamster Cell Mutants Deficient in Dihydrofolate Reductase Activity'. 1980 Genetics vol. 77 No. 7 pp. 4216-4220.
Verhoeyen et al., 'Reshaping Human Antibodies: Grafting an Antilysozyme Activity'. 1988 Science vol. 239 pp. 1534-1536.
Ward et al., 'Binding Activities of a Repertoire of Single Immunoglobulin Variable Domains Secreted from *Escherichia coil*'. 1989 Nature vol. 341 pp. 544-546.

* cited by examiner

Figure 2

| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| kabat | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VH seq | E | V | K | L | V | E | S | G | G | G | L | V | Q | P | G | G | S | R | K | L | S | C | A |

| position | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|---|---|
| kabat | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
| VH seq | A | S | A | F | T | F | S | S | F | G | M | H | W | V | R | Q | A | P | G | E | G | L | E |

| position | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|---|---|---|---|---|---|---|
| kabat | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 68 |
| VH seq | W | V | A | Y | I | S | S | G | S | S | T | I | Y | Y | A | D | T | V | K | G | R | F | T |

| position | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|
| kabat | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 |
| VH seq | I | S | R | D | N | P | K | N | T | L | F | L | Q | M | G | S | L | R | S | E | D | T | A |

| position | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|---|---|---|---|---|---|---|---|
| kabat | 89 | 90 | 91 | 92 | 93 | 94 | 95 | 96 | 97 | 98 | 99 | 100 | 101 | 102 | 103 | 104 | 105 | 106 | 107 | 108 | 109 | 110 |
| VH seq | M | Y | Y | C | A | R | P | Q | L | G | L | G | K | Q | G | T | T | I | D | T | L | T |

| position | 116 | 117 | 118 |
|---|---|---|---|
| kabat | 111 | 112 | 113 |
| VH seq | V | S | S |

Figure 3

| | | | | evklvesgggvlqpggsrklscaasgftfsdyemvwvrqapgeglewvayissgsrtihyadtvkgrftisrdnpkntlflqmsslrsedtamyycar | Reference sequence | |
|---|---|---|---|---|---|---|
| ..q.. | ..lr.. | | | ..s..s.n........k....s....s.s..y...s.........a..s..y...n...d....v... | VH3-48 | 81.6% 98 |
| ..q.. | ..k... | ..lr.. | | ..s..s.n........k....ss...s.sy..y...s.........a..s..y...n...a....v... | VH3-21 | 78.6% 98 |
| ..q.. | ..k... | ..lr.. | | ........y.s.i...k....s....sqs..y...s.........a..s..y...n...a....v... | VH3-11 | 78.6% 98 |
| ..q.. | ..r... | ..lr.. | | ..d...a.h.......k....s....sg..wn.gs.g...s.........a..s..y...n...a....l....k | VH3-09 | 76.5% 98 |
| ..q.. | | ..lr.. | | ..s..w.h.......k..v..sr.n.dgssts...........a.....y...n...a....v... | VH3-74 | 76.5% 98 |
| ..q.. | ..v... | ..lr.. | | ..s..a.h.......k....v..ydgsnky...s.........y.....n...a....v... | VH3-30.3 | 75.5% 98 |

| | | | | | | |
|---|---|---|---|---|---|---|
| ..q.. | | ..lr.. | | ..s..w.s.......k....n.kqdgseky.v.s.........a..s..y...n...a....v... | VH3-07 | 75.5% 98 |
| ..q.. | | ..lr.. | | ..s..a.h.......k...y.sa...nggsty..ns.........s.....y...g...a..m.v... | VH3-64 | 75.5% 98 |
| ..q.l.. | | ..lr.. | | ..s..a.s.......k....sa...csggsty...s.........s.....y...n...a....v....k | VH3-23 | 75.5% 98 |
| ..q.. | | ..lr.. | | ..s..a.h.......k...y.sa...nggsty...s.........s.....y...g...a..m.v... | VH3_64 | 75.5% 98 |
| ..q.. | ..e... | ..lr.. | | ..s..g.h.......k....v..ydgsnky...s.........s.....y...n...a....v... | VH3_30 | 75.5% 98 |
| ..q.. | ..v... | ..r.lr.. | | ..s..g.h.......k....v..wydgsnky...s.........s.....y...n...a....v... | VH3-33 | 74.5% 98 |
| ..q.. | ..v... | ..r.lr.. | | ..s..g.h.......k....v..ydgsnky...s.........s.....y...n...a....v....k | VH3-30 | 74.5% 98 |
| ..q.. | ..vv.. | ..lr.. | | ..d..t..h.......k....sl..wdggsty...s.........s..s..y...n...t...l..a... | VH3-43 | 73.5% 98 |
| ..q.. | ..v.r. | ..lr.. | | ..d..g.s........k....sg..nwnggstg...s.........a..s..y...n...a....l.h... | VH3-20 | 72.4% 98 |
| q.q.. | ..aevkk.. | .a.v..k.. | .y..ts.y.h... | .q....mgi..npsggsts..qkfq..v.mt..tsts.vymel.........v... | VH1-46 | 53.1% 98 |
| q.q.. | ..aevkk.. | .a.v..v.. | .y..ts.a.h... | .qr...mgw.na.ngntk.sqkfq..v..t..tsas.aymel.........v... | VH1-03 | 53.1% 98 |
| q.q.. | ..aevkk.. | .a.v..v.. | .y..tg.y.h... | .q....mgw.npn.ggtn..qkfq..v.mt..tsis.aymel.r....d..v... | VH1-02 | 52.0% 98 |
| q.q.. | ..aevkk.. | .a.v..k.. | .y..ts.a.h... | .qr...mgwsna.ngntk.sqefq..v..t..tsas.aymel........m.v... | VH1_3 | 51.0% 98 |
| qmq.. | .q..pevkk.. | .t.v..v.. | .y..k... | .r.qr..igw.vv..gntn..qkfqe.v..t..msts.aymel.........v....a | VH1_58 | 51.0% 98 |
| q.q.. | ..aevkk.. | .a.v..v.. | .y..ts.din... | .t.q...mgwmnpn.gntg..qkfq..v.mt.ntsis.aymel.........v... | VH1-08 | 50.0% 98 |
| qmq.. | .q..pevkk.. | .t.v..v.. | .y... | .r.qr..igw.vv..gntn..qkfqe.v..t..msts.aymel.........v... | VH1-58 | 50.0% 98 |
| qmq.. | .q..aevkkt. | .s.v..v.. | .y..tyrylh... | .qa....mgw.tpfngntn..qkfqd.v..t..rsms.aymel.........v....a | VH1-45 | 49.0% 98 |
| q.q.. | ..aevkk.. | .a.v..kv. | .y..itels.h... | ..k....mggfdpedgeti..qkfq..v.mte.tstd.aymel.........v....t | VH1-24 | 46.9% 98 |

10B3_vh.vh_1-3.ev_1.uniq range: 46.9% ~ 81.6%

Figure 4

| | Reference sequence | |
|---|---|---|
| JH3 | 81.8% | 11 |
| JH6 | 81.8% | 11 |
| JH1 | 81.8% | 11 |
| JH2 | 72.7% | 11 |

```
wgqgtiltvss
...mv......
...tv......
....lv.....
..r..lv....
```

Figure 6

| position | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| kabat | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| VH seq | E | V | K | L | V | E | S | G | G | G | L | V | Q | P | G | G | S | R | K | L | S | C | A |

| position | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|---|---|---|---|---|---|
| kabat | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 |
| VH seq | A | S | | | | | | | | | | | W | V | R | Q | A | P | G | E | G | L | E |

| position | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|---|---|---|---|---|---|---|
| kabat | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 |
| VH seq | W | V | A | | | | | | | | | | | | | | | | | | R | F | T |

| position | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 |
|---|---|---|---|---|---|---|---|---|---|---|---|---|---|---|---|---|---|---|---|---|---|---|---|
| kabat | 70 | 71 | 72 | 73 | 74 | 75 | 76 | 77 | 78 | 79 | 80 | 81 | 82 | 82a | 82b | 82c | 83 | 84 | 85 | 86 | 87 | 88 |
| VH seq | I | S | R | D | N | P | K | N | T | L | F | L | Q | M | S | S | L | R | S | E | D | T | A |

| position | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|---|---|---|---|---|---|---|---|
| kabat | 89 | 90 | 91 | 92 | 93 | 94 | 95 | | | | | | | | | | | | | | | | |
| VH seq | M | Y | Y | C | A | R | | | | | | | | | W | G | Q | G | T | E | L | L | T |

| position | 116 | 117 | 118 |
|---|---|---|---|
| kabat | 111 | 112 | 113 |
| VH seq | V | S | S |

Figure 7

| Germline | diff | fr_bm | avoid_bm |
|---|---|---|---|
| VH3-48 | 15 | 3 | 1 |
| VH3-21 | 18 | 3 | 1 |
| VH3-11 | 18 | 4 | 2 |
| VH3-07 | 19 | 2 | 0 |
| VH3-74 | 19 | 2 | 1 |
| VH3-64 | 19 | 3 | 1 |
| VH3_30 | 20 | 1 | 0 |
| VH3-30.3 | 20 | 1 | 0 |
| VH3-23 | 20 | 3 | 1 |
| VH3_64 | 20 | 3 | 1 |

Figure 8

```
                                                                                         Reference sequence
e.k.vesggglvqpgqsrkls..as.......apgeggewy.........................s.dpkn..qmsslrs.dtam.
..q............lr.......s.s.n....k..................s.s.y...s..............n..c....v..... VH3-48   81.6%   98
..q.k..........lr.......s.s.n....k..................s.sy.y...s..............n..a....v..... VH3-21   78.6%   98
q.q.k..........lr........y.s..........................sgs..y...s............n..a....v..... VH3-11   78.6%   98
..q...........r.lr.......d.a.h...k..................g..wn.gs.g.s...........n..a....l...k.. VH3-09   76.5%   98
..q............lr........s.w.h...k.v................r.n.dgssts.s...........n..a....v....... VH3-74   76.5%   98
q.q.v..........lr........s.a.h...k..................v..ydgsnky..s...........n..a....v....... VH3-30.3 75.5%   98
..q............lr........s.w.s...k..................n.kqdgseky.v.s..........n..a....v....... VH3-07   75.5%   98
..q............lr........s.a.h...k..................a..nggsty..ns...........g..a..m.v....... VH3-64   75.5%   98
..q.l..........lr........s.a.s...k..................a..gsggsty..s...........n..a....v...k.. VH3-23   75.5%   98
```

Figure 9

Table 1. IGHV genes and CNV

| IGHV1 subgroup | IGHV2 subgroup | IGHV3 subgroup | IGHV4 subgroup | IGHV5 subgroup | IGHV6 subgroup | IGHV7 subgroup |
|---|---|---|---|---|---|---|
| V1-2 (1-2)[45] | V2-70 (1-2)[8,41] | V3-9 (0-1)[37,38] | V4-30.1* (0-1)[2,28,33] | V5-a* (0-1)[26,40] | | V7-4.1* (0-1)[22,28] |
| V1-8 (0-1)[27,28] | | V3-11 (1-2)[45] | V4-30.2* (0-1)[2,28,33,41] | | | |
| V1-46 (1-2)[45] | | V3-23 (1-2)[5] | V4-30.4* (0-1)[2,28,33,41] | | | |
| V1-69 (1-2)[42,45] | | V3-30 (0-1)[49] | V4-31 (0-1)[45] | | | |
| V1-C* (0-1)[2,6] | | V3-30.3* (0-1)[2,28,33,41] | V4-39 (0-1)[39,1,52] | | | |
| V1-F* (0-1)[2,6] | | V3-30.5* (0-1)[2,28,33,41] | V4-59 (1-2)[45] | | | |
| | | V3-33 (0-1)[45] | V4-61 (0-1)[41,54] | | | |
| | | V3-53 (1-2)[8,40] | V4-b* (0-1)[2,6,28,33,40] | | | |
| | | V3-64 (1-2)[26] | | | | |
| | | V3-d* (0-1)[2,6] | | | | |

Abbreviations: CNV, copy number variation; IGHV, IG heavy chain variable gene cluster; IMGT, the international ImMunoGeneTics information system; ORF, open reading frame. Only functional and ORF genes found in CNV are shown (for all other genes, see IMGT locus representation[6,15], Figure 1). Asterisks denote IGHV genes not represented in the human reference assembly. Genes listed in the table without asterisks are found in the reference assembly in single copy. Numbers in parentheses signify predicted haploid copy number range for that IGHV gene. Selected references for each gene are also shown.

HIGH-THROUGHPUT ANTIBODY HUMANIZATION

RELATED APPLICATIONS

This application claims priority to U.S. Provisional Application No. 61/740,900 filed Dec. 21, 2012 and U.S. Provisional Application No. 61/783,999 filed Mar. 14, 2013, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 10, 2014, is named 553272 BBI-335_SL.txt and is 39,055 bytes in size.

FIELD OF THE INVENTION

The present invention relates to improved methods for antibody engineering, e.g., humanization.

BACKGROUND OF THE INVENTION

Rodent and other mammalian hybridomas are one of the primary sources of monoclonal antibodies. However, the development of rodent derived monoclonal antibodies as therapeutic antibodies is often hampered by the immunogenicity of rodent antibodies in humans. Antibody humanization technology is used to reduce immunogenicity triggered by non-human protein sequence in human while preserving antigen binding affinity and specificity.

Most of therapeutic antibodies are immunoglobulin G class molecules (IgG). One IgG molecule comprises two heavy chains and two light chains forming a heterotetramer "Y" shape molecule. IgG has two antigen-binding regions called Fab (fragment antigen binding) and one constant region called Fc (fragment crystalline). Each Fab region is a heterodimer of VH-CH1/VL-CL, where VH and VL of the Fv region are connected to the constant region of the heavy chain and the light chain, via linkers, respectively. These linkers allow the Fv considerable rotational flexibility. Each VH or VL has 3 hypervariable loops known as CDRs (complementarity determining regions) which sit at the tip of the Fv region. Three CDRs on VH or VL are connected by four framework regions (FRs 1-4). CDR residues are the key determinants of the antigen-binding properties of an antibody. Both heavy chain and light chain CDRs together form the antigen binding site. The heavy chain and light chain FRs constitute a scaffold for the antigen-binding site.

Antibody humanization is achieved by grafting CDRs of a rodent antibody onto a "similar" human framework (acceptor) and selecting minimal number of key framework residues (back-mutations) that are manually selected from a rodent monoclonal antibody and incorporated into human acceptor in order to maintain the original CDR conformation. Such methods are known in the art, and include those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567.

Although conventional antibody humanization is conducted according to these general principles, the choice of acceptor human framework(s) for grafting rodent CDRs as well as a minimal set of backmutations that retain optimal presentation of the CDRs while minimizing immunogenicity risk often varies from one antibody engineer to the other and requires a deep understanding of both immunoglobulin sequence/structure and antibody biology. Thus, antibody humanization is often a time-consuming and expensive process that adds significant expense to the development of a therapeutic antibody. Accordingly, there is an urgent need for improved humanization techniques that are more rapid and routine than conventional approaches.

SUMMARY OF THE INVENTION

This invention pertains to improved methods for humanizing non-human binding proteins, e.g, antibodies. In particular, the instant invention improves upon art-recognized humanization processes by providing a high-throughput antibody humanization process that can be automated in silico through computer-implementation. The methods of the invention significantly reduce the resources and time required for antibody humanization design, while also providing increased flexibility in screening. Moreover, and in contrast to conventional approaches which rely upon the obligatory selection of the most homologous human framework as an acceptor, the methods of the invention enable the antibody engineer to evaluate all possible human acceptors for selection and incorporation in a final humanization design.

In certain aspects, the disclosure provides a method of producing a humanized variant of a non human donor immunoglobulin comprising the steps of:

(i) providing a collection of all possible human immunoglobulin light chain variable region (VL) sequences or heavy chain variable region (VH) sequences with the same CDR canonical structures and Kabat subgroup assignment as the VL or VH sequence of the non-human donor immunoglobulin or a collection of acceptor sequences assembled according to a best-fit approach if no CDR canonical structure can be assigned;

(ii) for each acceptor sequence in the collection, identifying the number of non-identical residues at all framework region (FR) positions between the donor sequence and each acceptor sequence;

(iii) for each acceptor sequence in the collection, identifying the number of non-identical residues at key CDR positions ("strcdr") between the donor sequence and each acceptor sequence;

(iv) ranking the acceptor sequences in the collection based on a preference score ("diff") which is a sum of the number of non-identical residues identified in step (ii) and (iii) for each acceptor sequence;

(v) selecting the acceptor sequence in the collection with the lowest preference score;

(vi) synthesizing a DNA segment encoding a humanized VL or VH sequence comprising CDRs from the donor immunoglobulin engrafted in the variable region framework from the selected acceptor sequence; and comprising key FR amino acids from the donor immunoglobulin that replace non-identical amino acids at corresponding amino acid positions in the acceptor variable region framework;

(vii) introducing the DNA segment encoding the humanized VL or VH sequence and a DNA segment encoding a corresponding humanized VH or VL sequence into a cell; and (viii) expressing the DNA segments in the cell, thereby producing to produce a humanized variant of a non-human donor immunoglobulin.

In certain embodiments, the collection of all possible human immunoglobulin light chain variable region (VL) sequences is provided and the DNA segment encoding the humanized VL sequence is synthesized. In other embodiments, the collection of all possible human immunoglobulin heavy chain variable region (VH) sequences is provided and the DNA segment encoding the humanized VH sequence is synthesized.

In particular embodiments, the human light and/or heavy chain sequences comprise or consist of human germline sequences.

In certain embodiments, collection of all possible VH or VL germline acceptor sequences are selected from a complete human germline database comprising all or substantially all VH germline sequences from Table 3, all or substantially all Vkappa germline sequences from Table 4, or all or of substantially all Vlambda germline sequence from Table 5.

In certain embodiments, step (v) further comprises selecting the acceptor sequence in the collection with the lowest preference score and the lowest backmutation score ("fr_bm"), wherein the lowest backmutation score is established by:
(ix) providing a structural model of the donor immunoglobulin sequence;
(x) identifying all key FR residues in the VL or VH sequence of the non-human donor immunoglobulin which are (a) within about 5 Angstroms of the CDRs or VH/VL interface of the immunoglobulin and have a solvent exposure of less than 20% ("buried"); or (b) involved in the interaction with the CDR or another chain by specific hydrophobic, electrostatic or ion-ion chain interactions ("strltd"); and
(xi) for each acceptor sequence in the collection, identifying the number of non-identical residues at the key FR positions of step (x) between the donor sequence and each acceptor sequence to establish a total backmutation score ("fr_bm") for each acceptor sequence;
(xii) ranking the acceptor sequences in the collection based on the backmutation score;
(xiii) identifying the acceptor sequence in the collection with the lowest backmutation score.

In certain embodiments, step (v) further comprises assigning the acceptor sequences in the collection based on a germline subfamily classification and selecting the acceptor sequence based on its germline subfamily classification. In an embodiment, the germline subfamily classification is the Kabat germline subgroup designation for the acceptor sequence (e.g., VH1, VH2, VH3, VH4, VH5, VH6 or VH7 for a particular VH sequence, VK1, VK2, VK3, VK4, VK5 or VK6 for a particular VL kappa sequence, or VL1, VL2, VL3, VL4, VL5, VL6, VL7, VL8, VL9, or VL10 for a particular VL lambda sequence).

In certain embodiments, step (v) further comprises selecting the acceptor sequence in the collection with the lowest avoided backmutation ("avoid_bm") score, wherein lowest avoided backmutation scores are established by:
(xiv) for each acceptor sequence in the collection, identifying the total number of non-identical FR residues from step (ii) and step (xi) that are listed in Table 1 to establish an avoided backmutation score;
(xv) ranking the acceptor sequences in the collection based on the avoided backmutation score; and
(xvi) identifying the acceptor sequence in the collection with the lowest avoided backmutation score.

In certain embodiments, step (v) further comprises identifying the number of non-identical residues at all framework region (FR) positions between Framework Regions 1-3 (FR1-3) of the donor sequence and FR1-3 of each acceptor sequence.

In certain embodiments, the key CDR positions ("strcdr") are identified by:
(xvii) providing a structural model of the non-human donor immunoglobulin sequence;
(xviii) identifying all key FR residues in the VL or VH sequence of the non-human donor immunoglobulin which are involved in the interaction with the CDR or another chain by specific hydrophobic, electrostatic or ion-ion chain interactions ("strltd"); and
(xix) identifying all CDR positions having CDR residues which interact with the key FR residues identified in step (xviii).

In certain embodiments, the key FR amino acids from the donor immunoglobulin that replace the non-identical amino acids at corresponding FR positions in the selected acceptor variable region framework are identified by:
(xx) providing a structural model of the non-human donor immunoglobulin sequence;
(xxi) identifying all key FR residues ("strall"+"strltd") in the VL or VH sequence of the non-human donor immunoglobulin which are (a) within about 5 Angstroms of the CDRs or VH/VL interface of the donor immunoglobulin sequence ("strall") or (b) involved in the interaction with the CDR or another chain by specific hydrophobic, electrostatic or ion-ion chain interactions ("strltd");
(xxii) comparing the key FR residues of step (xxi) with the residues present at corresponding amino acid positions in the selected acceptor variable region framework to identify all key FR residues that are non-identical.

In certain embodiments, the key FR amino acids from the donor immunoglobulin that replace the non-identical amino acids at corresponding FR positions in the selected acceptor variable region framework are identified by:
(xx) providing a structural model of the non-human donor immunoglobulin sequence;
(xxi) identifying all key FR residues (v2="buried"+"strltd") in the VL or VH sequence of the non-human donor immunoglobulin which are (a) within about 5 Angstroms of the CDRs or VH/VL interface of immunoglobulin and have a solvent exposure of less than 20% ("buried") or (b) involved in the interaction with the CDR or another chain by specific hydrophobic, electrostatic or ion-ion chain interactions ("strltd");
(xxii) comparing the key FR residues of step (xxi) with the residues present at corresponding amino acid positions in the selected acceptor variable region framework to identify all key FR residues that are non-identical.

In certain embodiments, the key FR amino acids from the donor immunoglobulin that replace the non-identical amino acids at corresponding FR positions in the selected acceptor variable region framework are identified by:

(xx) providing a structural model of the non-human donor immunoglobulin sequence;

(xxi) identifying all key FR residues ("strltd") in the VL or VH sequence of the non-human donor immunoglobulin which are involved in the interaction with the CDR or another chain by specific hydrophobic, electrostatic or ion-ion chain interactions ("strltd");

(xxii) comparing the key FR residues of step (xxi) with the residues present at corresponding amino acid positions in the selected acceptor variable region framework to identify all key FR residues that are non-identical.

In certain embodiments, a humanized variant is selected that has the lowest sequence liability score of all possible humanized variants.

In certain embodiments, the humanized variant has an on rate constant ($K_{on}$) to its target antigen that is substantially the same or greater than the non-human donor immunoglobulin.

In certain embodiments, the DNA segment further comprises a linker polypeptide or an immunoglobulin constant domain. In one embodiment, the constant domain comprises an amino acid sequence selected from the group consisting of SEQ ID Nos:10-13.

In one embodiment, the binding protein is selected from the group consisting of: an immunoglobulin molecule, a disulfide linked Fv, a monoclonal antibody, a scFv, a chimeric antibody, a single domain antibody, a CDR-grafted antibody, a diabody, a humanized antibody, a multispecific antibody, a Fab, a dual specific antibody, a Fab', a bispecific antibody; a F(ab')2, or a Fv.

In another aspect, the invention provides a method for selecting a preferred antibody acceptor sequence in a collection of human antibody sequences comprising:

(i) providing a collection of all possible human immunoglobulin light chain variable region (VL) sequences and heavy chain variable region (VH) sequences with the same CDR canonical structures and Kabat subgroup assignment as the respective VL or VH sequence of the non-human donor immunoglobulin or a collection of acceptor sequences assembled according to a best-fit approach if no CDR canonical structure can be assigned;

(ii) for each acceptor sequence in the collection, identifying the number of non-identical residues at all framework region (FR) positions between the donor sequence and each said acceptor sequence;

(iii) for each acceptor sequence in the collection, identifying the number of non-identical residues at key CDR positions ("strcdr") between the donor sequence and each acceptor sequence;

(iv) ranking the acceptor sequences in the collection based on a preference score ("diff") which is a sum of the number of non-identical residues identified in step (ii) and (iii) for each said acceptor sequence; and (v) selecting the acceptor sequence in the collection with the lowest preference score;

wherein at least steps (ii) through (iv) are performed by a computer.

In one embodiment, the collection of all possible human immunoglobulin light chain variable region (VL) sequences is provided. In another embodiment, the collection of all possible human immunoglobulin heavy chain variable region (VH) sequences is provided. In another embodiment, the human VH or VL sequences are germline sequences.

In one embodiment, step (v) further comprises selecting the acceptor sequence in the collection with the lowest preference score and the lowest backmutation score ("fr_bm"), wherein the lowest backmutation score is established by:

(ix) providing a structural model of the donor immunoglobulin sequence;

(x) identifying all key FR residues in the VL or VH sequence of the non-human donor immunoglobulin which are (a) within about 5 Angstroms of the CDRs or VH/VL interface of the immunoglobulin and have a solvent exposure of less than 20% ("buried"); or (b) involved in the interaction with the CDR or another chain by specific hydrophobic, electrostatic or ion-ion chain interactions ("strltd"); and (xi) for each acceptor sequence in the collection, identifying the number of non-identical residues at the key FR positions of step (x) between the donor sequence and each acceptor sequence to establish a total backmutation score ("fr_bm") for each acceptor sequence;

(xii) ranking the acceptor sequences in the collection based on the backmutation score;

(xiii) identifying the acceptor sequence in the collection with the lowest backmutation score.

In one embodiment, step (v) further comprises selecting the acceptor sequence in the collection with the lowest avoided backmutation ("avoid_bm") score, wherein lowest avoided backmutation scores is established by:

(xiv) for each acceptor sequence in the collection, identifying the total number of non-identical FR residues from step (ii) and step (xi) that are listed in Table 1 to establish an avoided backmutation score;

(xv) ranking the acceptor sequences in the collection based on the avoided backmutation score; and (xvi) identifying the acceptor sequence in the collection with the lowest avoided backmutation score.

In certain embodiments, step (v) further comprises assigning the acceptor sequences in the collection based on a germline subfamily classification and selecting the acceptor sequence based on its germline subfamily classification. In an embodiment, the germline subfamily classification is the Kabat germline subgroup designation for the acceptor sequence (e.g., VH1, VH2, VH3, VH4, VH5, VH6 or VH7 for a particular VH sequence, VK1, VK2, VK3, VK4, VK5 or VK6 for a particular VL kappa sequence, or VL1, VL2, VL3, VL4, VL5, VL6, VL7, VL8, VL9, or VL10 for a particular VL lambda sequence).

In one embodiment, step (ii) comprises identifying the number of non-identical residues at all framework region (FR) positions between Framework Regions 1-3 (FR1-3) of the donor sequence and FR1-3 of each acceptor sequence.

In one embodiment, the key CDR positions ("strcdr") are identified by:

(vi) providing a structural model of the non-human donor immunoglobulin sequence;

(vii) identifying all key FR residues in the VL or VH sequence of the non-human donor immunoglobulin which are involved in the interaction with the CDR or another chain by specific hydrophobic, electrostatic or ion-ion chain interactions ("strltd"); and (viii) identifying all CDR positions having CDR residues which interact with the key FR residues identified in step (vii).

In one embodiment, the key FR amino acids from the donor immunoglobulin that replace the non-identical amino acids at corresponding FR positions in the selected acceptor variable region framework are identified by:
- (xx) providing a structural model of the non-human donor immunoglobulin sequence;
- (xxi) identifying all key FR residues (v1="strall"+ "strltd") in the VL or VH sequence of the non-human donor immunoglobulin which are (a) within about 5 Angstroms of the CDRs or VH/VL interface of the donor immunoglobulin sequence ("strall") or (b) involved in the interaction with the CDR or another chain by specific hydrophobic, electrostatic or ion-ion chain interactions ("strltd");
- (xxii) comparing the key FR residues of step (xxi) with the residues present at corresponding amino acid positions in the selected acceptor variable region framework to identify all key FR residues that are non-identical.

In one embodiment, the key FR amino acids from the donor immunoglobulin that replace the non-identical amino acids at corresponding FR positions in the selected acceptor variable region framework are identified by:
- (xx) providing a structural model of the non-human donor immunoglobulin sequence;
- (xxi) identifying all key FR residues ("buried"+"strltd") in the VL or VH sequence of the non-human donor immunoglobulin which are (a) within about 5 Angstroms of the CDRs or VH/VL interface of the immunoglobulin and have a solvent exposure of less than 20% ("buried") or (b) involved in the interaction with the CDR or another chain by specific hydrophobic, electrostatic or ion-ion chain interactions ("strltd");
- (xxii) comparing the key FR residues of step (xxi) with the residues present at corresponding amino acid positions in the selected acceptor variable region framework to identify all key FR residues that are non-identical.

In one embodiment, the key FR amino acids from the donor immunoglobulin that replace the non-identical amino acids at corresponding FR positions in the selected acceptor variable region framework are identified by:
- (xx) providing a structural model of the non-human donor immunoglobulin sequence;
- (xxi) identifying all key FR residues ("strltd") in the VL or VH sequence of the non-human donor immunoglobulin which are involved in the interaction with the CDR or another chain by specific hydrophobic, electrostatic or ion-ion chain interactions ("strltd");
- (xxii) comparing the key FR residues of step (xxi) with the residues present at corresponding amino acid positions in the selected acceptor variable region framework to identify all key FR residues that are non-identical.

In another aspect, the invention provides a method of producing a humanized variant of a non-human donor immunoglobulin comprising the steps of:
- (i) synthesizing a DNA segment encoding a humanized VL or VH sequence comprising CDRs from the donor immunoglobulin engrafted in the variable region framework from an acceptor sequence selected according to the method of the invention; and comprising key FR amino acids from the donor immunoglobulin that replace non-identical amino acids at corresponding amino acid positions in the acceptor variable region framework;
- (ii) introducing the DNA segment encoding the humanized VL or VH sequence and a DNA segment encoding a corresponding humanized VH or VL sequence into a cell; and
- (iii) expressing the DNA segments in the cell, thereby producing a humanized variant of a non-human donor immunoglobulin.

In another aspect, the invention provides a humanized variant of a non-human donor immunoglobulin produced according to the method of the invention. In one embodiment, said humanized variant has an on rate constant ($K_{on}$) to its target antigen that is substantially the same or greater than the non-human donor immunoglobulin.

In another embodiment, said DNA segment further comprises a linker polypeptide or an immunoglobulin constant domain. In another embodiment, the constant domain comprises an amino acid sequence selected from the group consisting of SEQ ID Nos:10-13. In another embodiment, said immunoglobulin is selected from the group consisting of: an immunoglobulin molecule, a disulfide linked Fv, a monoclonal antibody, a scFv, a chimeric antibody, a single domain antibody, a CDR-grafted antibody, a diabody, a humanized antibody, a multispecific antibody, a Fab, a dual specific antibody, a Fab', a bispecific antibody; a F(ab')2, or a Fv.

BRIEF DESCRIPTION OF THE INVENTION

FIG. 2 depicts VH Kabat numbering and CDR canonical structure assignment for the 10B3 rodent donor antibody (SEQ ID NO: 17). The location of amino acid insertions is indicated by a red circle.

FIG. 3 depicts a sequence alignment between the 10B3 VH donor sequence and a collection of 26 potential acceptor sequences with the same CDR canonical structure and Kabat subgroup assignment as the donor sequence (vh.1-3). Human germline sequences in vh.1-3 are ranked according to sequence identity to 10B3 VH. Identical residues in human germline sequences comparing with 10B3 VH are replaced by ".". Non-identical residues between 10B3 VH and human germline sequences are shown in letters. FIG. 3 lists SEQ ID NOS 28-52, respectively, in order of appearance.

FIG. 4 depicts an alignment of the 10B3 VH donor FR4 sequence with a collection of human germline JH FR4 sequences. FIG. 4 lists SEQ ID NOS 21, 3, 4, 1, and 2, respectively, in order of appearance.

Figure 5:
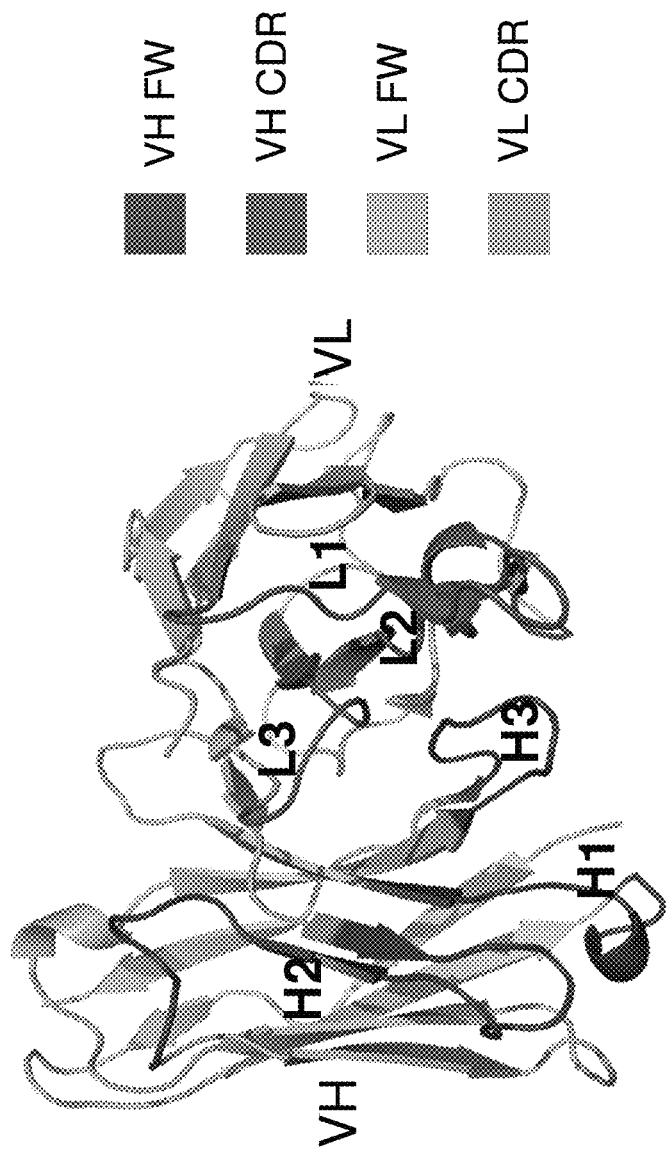

FIG. 5 depicts a structural model for rodent antibody 10B3.

FIG. 6 depicts key structural residues in rodent antibody 10B3 VH (SEQ ID NO: 17). These include buried (FR buried residues and 5 Å around CDRs), strltd (FR residues interacting with CDR or VL) and strcdr (CDR residues interacting with FR residue). Those positions are highlighted based on 10B3 VH sequence in cyan, yellow, and purple.

FIG. 7 depicts a ranking of the collection of human germline frameworks for the 10B3 VH acceptor framework.

FIG. 8 depicts backmutation sites on selected human germline framework for 10B3 VH ((VH 3-48), as well as other frameworks in the collection. The positions of backmutations on each human acceptor framework are highlighted in green. FIG. 8 SEQ ID NOS 28-37, respectively, in order of appearance.

FIG. 9 depicts exemplary "rare" VH germlines that may be included in certain optional embodiments of the invention.

DETAILED DESCRIPTION OF THE INVENTION

This invention pertains to improved methods for designing, e.g., humanizing, non-human binding proteins, particularly non-human antibodies, or antigen-binding portions thereof that bind an antigen of therapeutic interest.

Figure 1A:
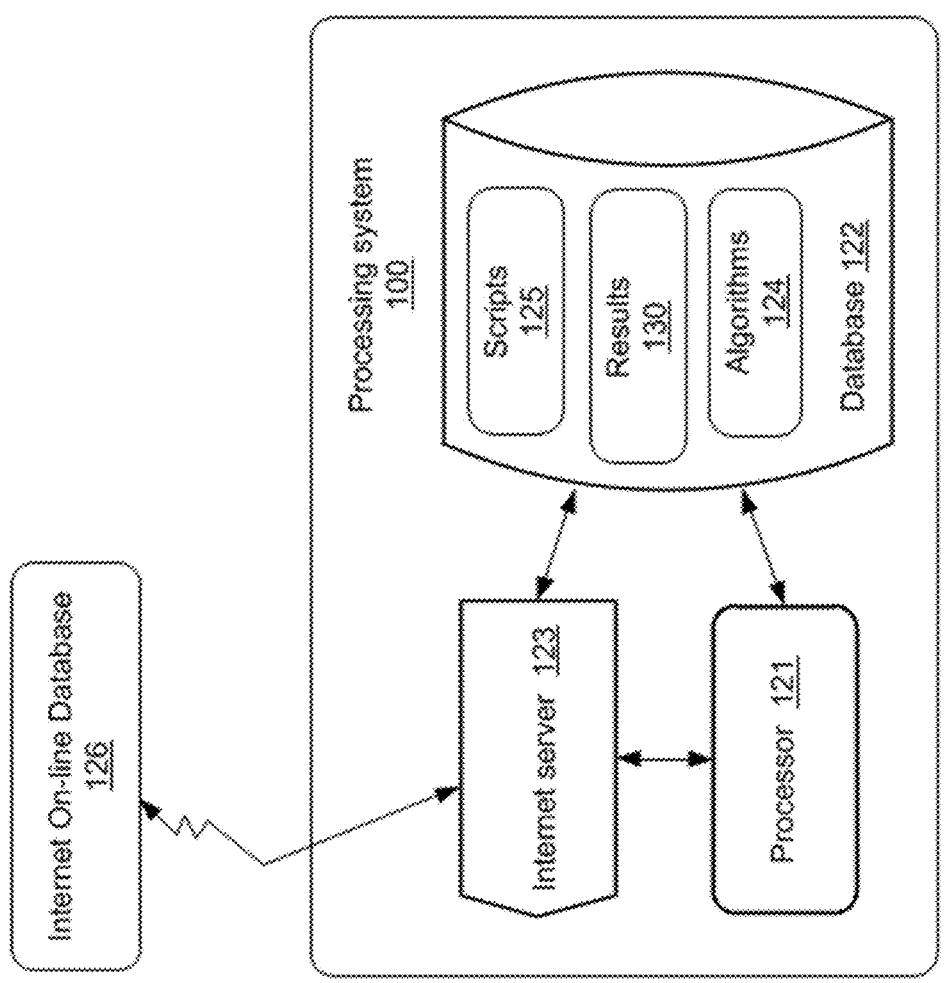
FIG. 1A depicts an exemplary computer system on which certain steps of the present methods are preformed.

FIG. 1A depicts an exemplary computer system 100 on which specific steps of the present methods may be performed. As shown in FIG. 1A, processing system 100 includes a processor 121, a local database 122, and an Internet server 123 for communicating with external databases, such as database 126, via the Internet. Local database 122 is used for storing scripts 125, intermediate and final results 130 of script execution, and algorithms 124.

Figure 1B:
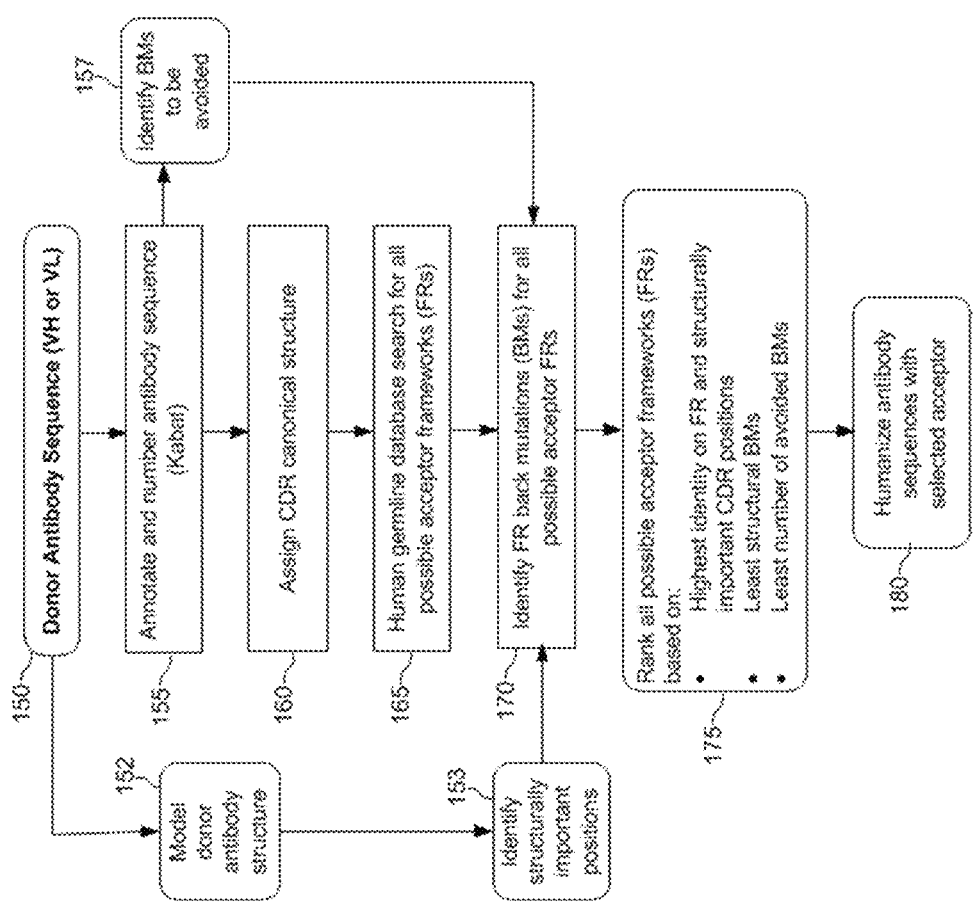
FIG. 1B depicts an exemplary workflow for high-throughput computer-aided antibody humanization design using the presently described methods.
Figure 1C:
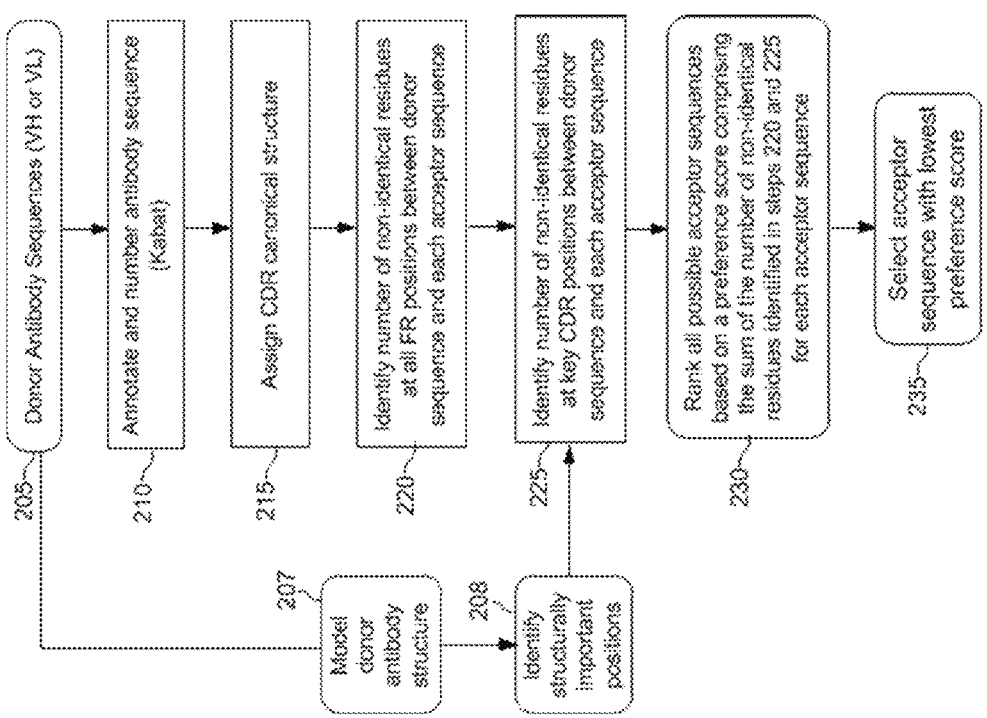
FIG. 1C is an exemplary flowchart showing steps performed in one embodiment of the present method.

FIG. 1B depicts an exemplary workflow for high-throughput computer-aided antibody humanization design using the presently described methods, and FIG. 1C is an exemplary flowchart showing steps performed in one embodiment of the present methods. FIGS. 1B and 1C are referenced below, throughout the description.

The methods of the invention can be substantially automated, e.g., using a web-based user interface. For example, a computer-implemented method of the invention can be conducted online by submitting sequence input file via a web portal. The humanized designs can be generated remotely using the computer-implemented methods of the invention and the results (e.g., candidate humanized antibody sequences) returned to the user via a website or email communication. One of skill in the art will recognize that the system and methods of the invention can be performed for multiple candidate antibodies either simultaneously or consecutively.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "binding protein" includes any protein or polypeptide capable of specific binding to a target protein. Binding proteins of the invention include, but are not limited to antibodies, antigen binding portions, and other antigen binding proteins capable of binding an antigen of interest.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., hPRLR). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art and represented in Table 1.

TABLE 1

Sequence of human IgG heavy chain constant domain and light chain constant domain

| Protein | Sequence Identifier | Sequence |
|---|---|---|
| | | 123456789012345678901234567890012 |
| | | 123456789012345678901234567890012 |
| Ig gamma-1 constant region | SEQ ID NO.: 10 | ASTKGPSVFFLAPSSKSTSGGTAALGOLVRDY FPEPVTVSWNSGALTSGVHTFPAVLQSSGLYS LSSVVTVPSSSLGTQTYICNVNHRPSNTKVOR KVEPKSCDKTHTCPPCPAPELLGGPSVPLPPP KPKDTLMISRTPEVTCVVVDVSHEDPEvKPNW YVDGVEVHNAKTRPREEQYNSTYRVVSVLTVL HQDWLNGKEYRCKVSNKALPAPIEKTISKAKG QPREPQVTTLPPSREEmTKNQVSLTCLVKGPT PSDIAVEWESNGQPENNYRTTPPvLDSDGSFP LYSKLTVDRSRWQQGNVPSCSVMHEALHNHYT QKSLSLSPGK |
| Ig gamma-1 constant region mutant | SEQ ID NO.: 11 | ASTKGPSVFPLAPSSKSTSGGTAALGCLVKDY FPEPVTVSWNSGALTSGVHTFPAVLQSSGLYS LSSVVTVPSSSLGTQTYIONVNHKPSNTKVDK KVEPKSCDKTHTCPPCPAPEAAGGPSVPLPPP KPKDTLMISRTPEVTCVVVDVSHEDPEVKPNW YVDGVEVHNAKTKPREEQYNSTYRVVSVLTVL HQDWLNGKETKCKvSNKALPAPIEKTISKAKG QPREPQVYTLPPSREEMTKNQVSLTCLVKGPY PSDIAVEWESNGQPENNYKTTPPVLDSDGSFP LYSKLTVDRSRWQQGNVFSCSVMHEALHNHYT QKSLSLSPGK |
| Ig Kappa constant region | SEQ ID NO.: 12 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |

TABLE 1-continued

Sequence of human IgG heavy chain constant domain and light chain constant domain

| Protein | Sequence Identifier | Sequence |
| --- | --- | --- |
| Ig Lambda constant region | SEQ ID NO.: 13 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds a desired target antigen is substantially free of antibodies that specifically bind antigens other than the desired target antigen). An isolated antibody that specifically binds a first target antigen may, however, have cross-reactivity to other target antigens, such as a related antigen from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) *Nucl. Acids Res.* 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad,*

Sci. 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., *J. Mol. Biol.* 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (*J Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FRE FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., *Crit. Rev. Immunol.* 22(3): 183-200 (2002); Marchalonis et al., *Adv Exp Med Biol.* 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, *J. Mol. Biol.* 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

As used herein, the term "neutralizing" refers to neutralization of biological activity of a cytokine receptor when a binding protein specifically binds the cytokine receptor. Preferably, a neutralizing binding protein is a neutralizing antibody whose binding to a target antigen results in inhibition of a biological activity of the target antigen. Preferably the neutralizing binding protein binds the target antigen and reduces a biologically activity of the target antigen by at least about 20%, 40%, 60%, 80%, 85% or more Inhibition of a biological activity by a neutralizing binding protein can be assessed by measuring one or more indicators of biological activity well known in the art. The term "activity" includes activities such as the binding specificity/affinity of an antibody for an antigen and/or the neutralizing potency of an antibody, e.g., inhibition of phosphorylation.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BlAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_D$", as used herein, is intended to refer to the dissociation constant of a particular antibody-antigen interaction as is known in the art.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as used herein refers to a polymeric form of two or more nucleotides, either ribonucleotides or deoxvnucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences
which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., WO 2007/014162 incorporated herein by reference).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

A. Providing a Non-Human Donor Antibody for Humanization

The methods of the invention employ a non-human donor monoclonal antibody as starting material. Such monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse or other rodent immunized with an antigen of the invention with myeloma cells and then screening the hybridomas resulting from the fusion for hybridoma clones that secrete an antibody able to bind a polypeptide of the invention. Briefly, mice can be immunized with a desired target antigen. In a preferred embodiment, the antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a target antigen, antibodies and/or antibody-producing cells may be obtained from the animal. Anti-antibody-containing serum is obtained from the animal by bleeding or sacrificing the animal. The serum may be used as it is obtained from the animal, an immunoglobulin fraction may be obtained from the serum, or the antibodies may be purified from the serum. Serum or immunoglobulins obtained in this manner are polyclonal, thus having a heterogeneous array of properties.

Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding the target antigen. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using the target antigen, or a portion thereof, or a cell expressing the target antigen. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

In another aspect of the invention, the donor antibody is generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described in Section 1, are screened using an antigen-specific hemolytic plaque assay, wherein the target antigen, or a subunit or a fragment thereof, is coupled to sheep red blood cells using a linker, such as biotin, and used to identify single cells that secrete antibodies with specificity for the target. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to the target antigen. The amplified immunoglobulin sequences further can be manipulated in vitro, such as by in vitro affinity maturation methods such as those described in PCT Publication WO 97/29131 and PCT Publication WO 00/56772.

In vitro methods also can be used to provide donor antibodies. For example, an antibody library may be screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with the target antigen, or a portion thereof, such as the extracellular domain. Alternatively, the recombinant antibody library may be from a naïve subject, i.e., one who has not been immunized with the target antigen, such as a human antibody library from a human subject who has not been immunized with the human antigen. Antibodies of the invention are selected by screening the recombinant antibody library with the peptide comprising human antigen to thereby select those antibodies that recognize the target. Methods for conducting such screening and selection are well known in the art, such as described in the references in the preceding paragraph. To select antibodies of the invention having particular binding affinities for a human target antigen, such as those that dissociate from the human target with a particular $k_{off}$ rate constant, the art-known method of surface plasmon resonance can be used to select antibodies having the desired $k_{off}$ rate constant. To select antibodies of the invention having a particular neutralizing activity, such as those with a particular an $IC_{50}$, standard methods known in the art for assessing the inhibition of target activity may be used.

In certain exemplary embodiment, parental antibodies can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780, 225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946, 778 and 5,258,498; Huston et al., *Methods in Enzymology* 203:46-88 (1991); Shu et al., *PNAS* 90:7995-7999 (1993); and Skerra et al., *Science* 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in Wittrup et al. (U.S. Pat. No. 6,699,658) incorporated herein by reference.

B. Design of Humanized Antibodies
i. Sequence Analysis of Non-Human Donor Antibody
   (1) Annotation of Donor Antibody Sequence Having sequenced VH and VL domains of the non-human (e.g., rodent) donor antibody, the amino acid sequences may be extracted and stored into a suitable sequence file format (e.g., FASTA) for sequence manipulation. In certain embodiments, the VH and VL sequence of the donor antibody are then annotated into component FR and CDR domains using a Hidden Markov Model (HMM). Hidden Markov models (HMM) are a highly effective means of modeling a family of unaligned sequences or a common motif within a set of unaligned sequences. For example, locally installed programs (e.g., HMMER, available from Janelia Farm Research, Ashburn, Va. may be used to generate HMMs for annotation of a VL or VH sequences into its component domains: FR1-CDR1-FR2-CDR2-FR3-CDR3-FR4. Antibody sequence annotation may generate separate segment sequence files for each component domain.

(2) Kabat Numbering of Donor Antibody Sequence

For each segment sequence file, a "kabat" file is generated (by processor 121, in one embodiment) in which every amino acid in each sequence segment is renumbered according to the Kabat numbering convention (see, http://www-.bioinf.org.uk/abs/#kabatnum), at steps 155 and 210, in FIGS. 1B and 1C, respectively. The Kabat numbering convention (see Table 1) provides appropriate correlation between antibody sequence and 3D protein structure and ensures that residues topologically equivalent among homologous family members will get the same number. Insertions in the numbering (for instance, at Kabat position 35A, 52A-C, etc) may be introduced to accommodate different lengths in CDR(s) or FR region(s). Accordingly, the "Kabat" sequence file may take the form of three columns in which one column provide the amino acids of the sequence segment file in sequential order, a second column provides the sequential numbering for each amino acid, and a third column provides the corresponding Kabat numbering for each amino acid.

TABLE 1

Antibody sequence Kabat numbering scheme

| Chain | Fragment | Kabat Number | Potential Insertion |
|---|---|---|---|
| VH | FR1 | 1-25 | |
| | CDR1 | 26-35B | 35, 35A |
| | FR2 | 36-49 | |
| | CDR2 | 50-65 | 52A-C |
| | FR3 | 66-94 | 82A-C |
| | CDR3 | 95-102 | 100A-K |
| | FR4 | 103-113 | |
| VK | FR1 | 1-23 | |
| | CDR1 | 24-34 | 27A-F |
| | FR2 | 35-49 | |
| | CDR2 | 50-56 | |
| | FR3 | 57-88 | |
| | CDR3 | 89-97 | 95A-F |
| | FR4 | 98-109 | 106A |

(3) Assigning CDR Canonical Structure to Donor Antibody Sequence

The CDRs of each annotated and renumbered VH or VL are then analysed (in one embodiment, by processor 121) to assign CDRs to one of several known CDR canonical structures, at steps 160 and 215, in FIGS. 1B and 1C, respectively. The CDR canonical structure class was introduced by Chothia and co-workers to allow a direct prediction of CDR conformation from sequence (see Chothia et al., J. Mol. Biol. 196 (1987) 901-917; Chothia et. al., J. Mol. Biol. 227 (1992), 799-817; Tomlinson, et al., EMBO J. 14 (1995) 4628-4638; Martin et al., J. Mol. Biol. 263 (1996) 800-815; Al-Lazikani, et al.; J. Mol. Biol. 273 (1997). The most important features of canonical structure determination for 5 of 6 CDRs (VH CDR1-2 and VL CDR1-3) are listed in Table 2. Kabat numbering scheme is used. Accordingly, CDR canonical structures may be assigned for based on the criteria listed in Table 2.

TABLE 2

CDR canonical structure determination criteria

| Chain | CDR | Canonical structure | CDR length | Residue at Critical Position (Kabat number) |
|---|---|---|---|---|
| VH | CDR1 | 1 | 10 | |
| | | 2 | 11 | |
| | | 3 | 12 | |
| | CDR2 | 1 | 16 | |
| | | 2 | 17 | 52a = P/S or 55 = G/S and 71 = A/V/L/I/T |
| | | 3 | 17 | 54 = G/S/N/D and 71 = R/K |
| | | 4 | 19 | |
| | | 5 | 18 | |
| | | 6 | 15 | |
| VK | CDR1 | 1 | 10 | |
| | | 2 | 11 | |
| | | 3 | 17 | |
| | | 4 | 16 | |
| | | 5 | 15 | |
| | | 6 | 12 | |
| | CDR2 | 1 | 7 | |
| | CDR3 | 1 | 9 | |
| | | 3 | 8 | |
| | | 5 | 10 | | ii. Assembling a Collection of Human Acceptor Germline Sequences (1) Human Germline Database Consolidation and CDR Canonical Structure Assignment Potential human acceptor sequences for the CDRs of the donor VH or VL sequence may be compiled from databases of human IG germline sequences or other human acceptor sequences, e.g., at step 165.

Known human Ig sequences are disclosed, e.g., www.ncbi.nlm.nih gov/entrez-/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.htm; www.library-.thinkquest.org/12429/Immune/Antibody.html; www.hhmi-.org/grants/lectures/1996/vlab/; www.path.cam.ac.uk/.about.mrc7/m-ikeimages.html; www.antibodyresource.com/; mcb.harvard.edu/BioLinks/Immuno-logy.html.www.immunologylink.com/; pathbox-.wustl.edu/.about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Elisa.html; www-.biodesign.com/table.asp; www.icnet.uk/axp/facs/davies/links.html; www.biotech.ufl.edu/.about.fccl/protocol.html; www.isac-net.org/sites_geo.html; aximtl.imt.uni-marburg.de/.about.rek/AEP-Start.html; baserv.uci.kun.nl/.about.jraats/linksl.html; www.recab.uni-hd.de/immuno.b-me.nwu.edu/; www.mrc-cpe.cam.ac.uk/imt-doc/pu-blic/INTRO.html; www.ibt.unam.mx/vir/V_mice.html; imgt.cnusc.fr:8104/; www.biochem.ucl.ac.ucl.ac.uk/.about-.martin/abs/index.html; antibody.bath.ac.uk/; abgen.cvm.tamu.edu/lab/wwwabgen.html; www.unizh.ch/.about.honegger/AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.abo-ut.fmolina/Webpages/Pept/spottech.html; www.jerini.de/frroducts.htm; www.patents.ibm.com/ibm.html.Kabat et al., Sequences of Proteins of Immunological Interest, U.S. Dept. Health (1983), each entirely incorporated herein by reference.

In certain preferred embodiments, the methods of the invention employ a human germline sequence database compiled from publically available databases such as Vbase (http://vbase.mrc-cpe.cam.ac.uk/) and NCBI (www.ncbi.nlm.nih gov/) and IMGT (http://www.imgt.org/). The Vbase, NCBI, and IMGT designations for exemplary human VH, Vkappa, and VLambda sequences are provided in Tables 3, 4 and 5, respectively. In certain embodiments, the human germline sequence database comprises all, or substantially all (e.g., more than 75%, 80%, 85%, 90% or 95%) of the 61 unique VH germline sequences from Table 3. In other embodiments, the germline database of the invention comprises all, or substantially all (e.g., more than 75%, 80%, 85%, 90% or 95%)) of the 36 Vkappa germline sequence listed in Table 4. In other embodiments, the germline database of the invention comprises all, or substantially all (e.g., more than 75%, 80%, 85%, 90% or 95%) of the 31 Vlambda germline sequences listed in Table 5. In other embodiments, the germline databases of the invention specifically exclude human germline sequences comprising free cysteine residues or human germline sequences that are missing conservative cysteine residues.

TABLE 3

Human VH germline sequences

| Vbase | NCBI | IMGT |
|---|---|---|
| VH1-02 | VH1_2 | IGHV1-2*02 (F) |
| VH1-03 | | IGHV1-3*01 (F) |
| | VH1_3 | IGHV1-3*02 (F) |
| VH1-08 | VH1_8 | IGHV1-8*01 (F) |
| VH1-18 | VH1_18 | IGHV1-18*01 (F) |
| VH1-24 | VH1_24 | IGHV1-24*01 (F) |
| VH1-45 | VH1_45 | IGHV1-45*01 (F), IGHV1-45*02 (F) |
| VH1-46 | VH1_46 | IGHV1-46*01 (F), IGHV1-46*03 (F) |
| VH1-58 | | IGHV1-58*01 (F) |
| | VH1_58 | IGHV1-58*02 (F) |
| VH1-69 | | IGHV1-69*01 (F), IGHV1-69*12 (F), IGHV1-69*13 ((F)) |
| VH1-e | VH1_69 | IGHV1-69*06 (F) |
| VH1-f | | IGHV1-f*01 (F) |
| VH2-05 | VH2_5 | IGHV2-5*01 (F) |
| VH2-26 | VH2_26 | IGHV2-26*01 (F) |
| VH2-70 | | IGHV2-70*04 (F) |
| | VH2_70 | IGHV2-70*01 (F), IGHV2-70*13 (F) |
| VH3-07 | VH3_7 | IGHV3-7*01 (F), IGHV3-7*02 (F) |
| VH3-09 | VH3_9 | IGHV3-9*01 (F) |
| VH3-11 | VH3_11 | IGHV3-11*01 (F) |
| VH3-13 | VH3_13 | IGHV3-13*01 (F) |
| VH3-15 | VH3_15 | IGHV3-15*01 (F), IGHV3-15*05 (F) |
| VH3-20 | VH3_20 | IGHV3-20*01 (F) |
| VH3-21 | VH3_21 | IGHV3-21*01 (F), IGHV3-21*02 (F) |
| VH3-23 | VH3_23 | IGHV3-23*01 (F) |
| VH3-30, VH3-30.5 | | IGHV3-30*18 (F), IGHV3-30*04 (F) |
| | VH3_30 | IGHV3-30*03 (F), IGHV3-30*06 (F), IGHV3-30*12 (F), IGHV3-30*19 (F), IGHV3-33*05 (F) |
| VH3-30.3 | | IGHV3-30-3*01 (F), IGHV3-30*01 (F), IGHV3-33*04 (F), IGHV3-30*07 (F), IGHV3-30*11 (F), IGHV3-30*14 (F), IGHV3-30*16 (F), IGHV3-30*17 (F) |
| VH3-33 | VH3_33 | IGHV3-33*01 (F) |
| VH3-43 | VH3_43 | IGHV3-43*01 (F) |
| VH3-48 | VH3_48 | IGHV3-48*02 (F) |
| VH3-49 | | IGHV3-49*01 (F) |
| | VH3_49 | IGHV3-49*03 (F) |
| VH3-53 | | IGHV3-53*02 (F) |
| | VH3_53 | IGHV3-53*01 (F) |
| VH3-64 | | IGHV3-64*01 (F) |
| | VH3_64 | IGHV3-64*02 (F) |
| VH3-66 | | IGHV3-66*01 (F), IGHV3-66*02 (F), IGHV3-66*04 (F) |
| | VH3_66 | IGHV3-66*03 (F) |
| VH3-72 | VH3_72 | IGHV3-72*01 (F) |
| VH3-73 | VH3_73 | IGHV3-73*01 (F), IGHV3-73*02 (F) |
| VH3-74 | VH3_74 | IGHV3-74*01 (F), IGHV3-74*02 (F) |
| VH3-d | | IGHV3-d*01 (F) |
| VH4-04 | | IGHV4-4*02 (F) |
| | VH4_4 | IGHV4-4*07 (F) |
| VH4-28 | VH4_28 | IGHV4-28*01 (F), IGHV4-28*03 (F) |
| VH4-30.1, VH4-31 | VH4_31 | IGHV4-31*02 (F), IGHV4-31*03 (F) |
| VH4-30.2 | | IGHV4-30-2*01 (F) |
| VH4-30.4 | | IGHV4-30-4*01 (F) |
| VH4-34 | VH4_34 | IGHV4-34*01 (F), IGHV4-34*02 (F) |
| VH4-39 | VH4_39 | IGHV4-39*01 (F) |
| VH4-59 | VH4_59 | IGHV4-59*01 (F) |
| VH4-61 | | IGHV4-61*01 (F) |
| | VH4_61 | IGHV4-61*08 (F) |
| VH4-b | | IGHV4-b*01 (F) |
| VH5-51 | VH5_51 | IGHV5-51*01 (F), IGHV5-51*03 (F) |
| VH5-a | | IGHV5-a*01 (F), IGHV5-a*03 (F) |
| VH6-01 | VH6_1 | IGHV6-1*01 (F), IGHV6-1*02 (F) |
| VH7-4.1 | VH7_4.1 | IGHV7-4-1*01 (F) |
| | VH3_16 | IGHV3-16*01 (ORF), IGHV3-16*02 (ORF) |
| | VH3_35 | IGHV3-35*01 (ORF) |
| | VH3_38 | IGHV3-38*02 (ORF) |
| | VH7_81 | IGHV7-81*01 (ORF) |

TABLE 4

Human VKappa germline sequences

| Vbase | NCBI | IMGT |
|---|---|---|
| VK1-A20 | A20 | IGKV1-27*01 (F) |
| VK1-A30 | A30 | IGKV1-17*01 (F) |
| VK1-L1 | L1 | IGKV1-16*01 (F) |
| VK1-L11 | L11 | IGKV1-6*01 (F) |
| VK1-L12 | L12 | IGKV1-5*01 (F) |
| VK1-L14 | L14 | IGKV1D-17*01 (F) |
| VK1-L15 | L15 | IGKV1D-16*01 (F) |
| VK1-L23 | L23 | IGKV1D-43*01 (F) |
| VK1-L24 | L24 | IGKV1D-8*01 (F) |
| VK1-L4, VK1-L18 | L18, L4_18a | IGKV1-13*02 (F), IGKV1D-13*01 (F) |
| VK1-L5, VK1-L19 | L19, L5 | IGKV1-12*01 (F), IGKV1-12*02 (F), IGKV1D-12*01 (F), IGKV1D-12*02 (F) |
| VK1-L8 | L8 | IGKV1-9*01 (F) |
| VK1-L9 | L9 | IGKV1-8*01 (F) |
| VK1-O12, VK1-O2 | O12, O2 | IGKV1-39*01 (F), IGKV1D-39*01 (F) |
| VK1-O18, VK1-O8 | O18, O8 | IGKV1-33*01 (F), IGKV1D-33*01 (F) |
| VK2-A1 | A1 | IGKV2D-30*01 (F) |
| VK2-A17 | A17 | IGKV2-30*01 (F) |
| VK2-A18 | | IGKV2-29*02 (F), IGKV2-29*03 (F) |
| VK2-A19, VK2-A3 | A19, A3 | IGKV2-28*01 (F), IGKV2D-28*01 (F) |
| VK2-A2 | A2 | IGKV2D-29*01 (F) |
| VK2-A23 | A23 | IGKV2-24*01 (F) |
| VK2-O11, VK2-O1 | O1, O11 | IGKV2-40*01 (F), IGKV2D-40*01 (F) |
| VK3-A11 | A11 | IGKV3D-20*01 (F) |
| VK3-A27 | A27 | IGKV3-20*01 (F) |
| VK3-L2, VK3-L16 | L2 | IGKV3-15*01 (F), IGKV3D-15*01 (F) |
| VK3-L20 | L20 | IGKV3D-11*01 (F) |
| VK3-L25 | L25 | IGKV3/OR2-268*01, IGKV3/OR2-268*02, IGKV3D-7*01 (F) |
| VK3-L6 | L6 | IGKV3-11*01 (F) |
| VK4-B3 | B3 | IGKV4-1*01 (F) |
| VK5-B2 | B2 | IGKV5-2*01 (F) |
| VK6-A14 | A14 | IGKV6D-41*01 (ORF) |
| VK6-A26, VK6-A10 | A10, A26 | IGKV6-21*01 (ORF), IGKV6D-21*01 (ORF) |
| | O14, O4 | IGKV1-37*01 (ORF), IGKV1D-37*01 (ORF) |
| | L22 | IGKV1D-42*01 (ORF) |
| | A7 | IGKV2D-24*01 (ORF) |
| | L10 | IGKV3-7*01 (ORF) |
| | A5 | IGKV2D-26*01 |

TABLE 5

Human VLambda germline sequences

| Vbase | IMGT |
|---|---|
| VL1-1a | IGLV1-36*01 (F) |
| VL1-1b | IGLV1-51*01 (F) |
| VL1-1c | IGLV1-44*01 (F) |
| VL1-1e | IGLV1-40*01 (F) |
| VL1-1g | IGLV1-47*01 (F) |
| VL2-2a2 | IGLV2-14*01 (F) |
| VL2-2b2 | IGLV2-23*02 (F) |
| VL2-2c | IGLV2-8*01 (F) |
| VL2-2d | IGLV2-18*01 (F), IGLV2-18*02 (F) |
| VL2-2e | IGLV2-11*01 (F), IGLV2-11*02 (F) |
| VL3-219 | IGLV3-27*01 (F) |
| VL3-3a | IGLV3-16*01 (F) |
| VL3-3e | IGLV3-22*01 (F) |
| VL3-3h | IGLV3-21*01 (F) |
| VL3-3j | IGLV3-9*01 (F) |
| VL3-3l | IGLV3-19*01 (F) |
| VL3-3m | IGLV3-25*01 (F) |
| VL3-3p | IGLV3-10*01 (F) |
| VL3-3r | IGLV3-1*01 (F) |
| VL4-4a | IGLV4-60*01 (F) |
| VL4-4b | IGLV4-69*01 (F), IGLV4-69*02 (F) |
| VL4-4c | IGLV4-3*01 (F) |
| VL5-5b | IGLV5-52*01 (F) |
| VL5-5c | IGLV5-45*01 (F) |
| VL5-5e | IGLV5-37*01 (F) |
| VL6-6a | IGLV6-57*01 (F) |
| VL7-7a | IGLV7-43*01 (F) |
| VL7-7b | IGLV7-46*01 (F) |
| VL8-8a | IGLV8-61*01 (F) |
| VL9-9a | IGLV9-49*01 (F), IGLV9-49*02 (F), IGLV9-49*03 (F) |
| VL10-10a | IGLV10-54*01 (F) |

In certain optional embodiments, the human germline sequence database of the invention further comprises at least one additional "rare" VH germline that is less represented in in the human genome. Exemplary "rare" germlines are depicted in FIG. 9. For example, the human database may comprises one or more, all, or substantially all (e.g., more than 75%, 80%, 85%, 90% or 95%) of the VH germline sequences from one of the Kabat subgroups depicted in FIG. 9. Although less preferred for antibody humanization design, one or more of these "rare" germlines can be incorporated into the acceptor ranking process of the invention in certain optional embodiments.

In the methods of the invention, the CDRs of each VH or VL (Vkappa or Vlambda) sequence in the germline sequence database may be analysed to assign a CDR canonical structure according to the criteria summarized in Table 2. Moreover, in certain embodiments, human germline sequences may be assigned to one of several Kabat subgroups according to their CDR canonical structures as shown in Table 6.

TABLE 6

Human germline CDR canonical structure assignment

| Chain | CDR Canonical Structure# | Germline | Number of human frame work | Unique germline sequence[α] |
|---|---|---|---|---|
| VH | vh.1-1 | VH3, VH4 | 7 | VH3-13, VH3-53, VH3-66, VH4_4*, VH4-34, VH5-59, VH3_53* |
| | vh.1-2 | VH1, VH5, VH7 | 8 | VH1-18, VH1-e, VH1-69, VH1-f, VH5-51, VH5-a, VH7-4.1, VH7_81* |
| | vh.1-3 | VH1, VH3 | 26 | VH1-02, VH1-03, VH1-08, VH1-24, VH1-45, VH1-46, VH1-58, VH3-07, VH3-09, VH3-11, VH3-20, VH3-21, VH3-23, VH3-30, VH3-30.3, VH3-33, VH3-43, VH3-48, VH3-64, VH3-74, VH1_3*, VH1_58*, VH3_30*, VH3_64*, VH3_16*, VH3_35* |
| | vh.1-4 | VH3 | 4 | VH3-72, VH3-73, VH3-15, VH3-49 |

TABLE 6-continued

Human germline CDR canonical structure assignment

| Chain | CDR Canonical Structure# | Germline | Number of human frame work | Unique germline sequence$^a$ |
|---|---|---|---|---|
| | vh.1-6 | VH3 | 2 | VH3-d, VH3_38* |
| | vh.2-1 | VH2, VH4 | 3 | VH4-04, VH4-28, VH4-b |
| | vh.3-1 | VH2, VH4 | 10 | VH2-05, VH2-26, VH2-70, VH4-31, VH4-30.2, VH4-30.4, VH4-39, VH4-61, VH3_49*, VH4_61* |
| | vh.3-5 | VH6 | 1 | VH6-01 |
| VK | vk.2-1-1 | VK1, VK3, VK5, VK6 | 23 | VK1-O12, VK1-O18, VK1-A30, VK1-L14, VK1-L1, VK1-L15, VK1-L18, VK1-L5, VK1-L8, VK1-L23, VK1-L9, VK1-L11, VK3-L2, VK3-L6, VK5-B2, VK6-A10, VK6-A14, VK1-A20, VK1-L12, VK3-L20, VK1-L24, VK1_O14*, VK1_L22* |
| | vk.3-1-1 | VK2, VK4 | 2 | VK2-O11, VK4-B3 |
| | vk.4-1-1 | VK2 | 7 | VK2-A17, VK2-A1, VK2-A18, VK2-A2, VK2-A3, VK2-A23, VK2_A5*. |
| | vk.6-1-1 | VK3 | 4 | VK3-A27, VK3-A11, VK3-L25, VK3_L10* |

CDR canonical structure classification is provided for CDR1-CDR2 of VH and CDR1-CDR2-CDR3 of VL. For example, vh.1-2 means that VH has canonical structure 1 for CDR1 and canonical structure 2 for CDR2;
vk.2-1-1 means that VL has canonical structure 2 for CDR1,, canonical structure 1 for CDR2, and canonical structure 1 for CDR3.
*Human germline sequence in NCBI but not in Vbase
$^a$VH3-30 = VH3-30.5; VH4-31 = VH4-30.1; VK1-L4 = VK1-L18; VK1-L5 = VK1-L19; VK1-O12 = VK1-O2; VK1-O18 = VK1-O8; VK2-A19 = VK2-A3; VK2-O11 = VK2-O1; VK3-L2 = VK3-L16; VK6-A26 = VK6-A10, VK1_O14* = VK1_O4*

(2) Assembling Potential Acceptor Sequences

At steps 150 and 205, shown in FIGS. 1B and 1C, respectively, the CDR canonical structure and Kabat subgroup assignment of the non-human donor immunoglobulin is referenced to identify a collection of all possible human germline immunoglobulin light chain variable region (VL) sequences or heavy chain variable region (VH) sequences with the same CDR canonical structures and Kabat subgroup assignment as the corresponding sequences of the donor immunoglobulin. Only the human germline amino acid sequences in the subgroup with the same CDR canonical structure as the donor antibody are further considered as the potential acceptor human framework.

If donor CDR canonical structures cannot be successfully assigned or if no human germline can adopt the same CDR canonical structures, searching for potential acceptor human framework(s) is carried out using the complete human germline database defined above. For example, if the heavy or light chain CDR canonical structure of non-human donor immunoglobulin cannot be assigned based on the criteria listed in Table 2, the VL or VH acceptor sequence searching is extended to consider all (or substantially all, e.g., more than 75%, 80%, 85%, 90% or 95%)) of VL or VH germline sequences, e.g., all (or substantially all) of the VH germline sequences listed Table 3, all (or substantially all) of the Vkappa sequence in Table 4, and/or all (or substantially all) of the Vlambda sequences in Table 5, using a "best-fit" approach.

According to a "best fit" approach, the sequence of the non-human donor immunoglobulin VL or VH (e.g., FR1+CDR1+FR2+CDR2+FR3) is aligned against all (or substantially all) of the sequences in the human VL (Vkappa or Vlambda) or VH germline database. Germline sequences with minimal framework residue differences (e.g., 3 or less) from the non-human donor immunoglobulin are then selected as possible human acceptor sequences. These acceptor sequences may be subgrouped based on framework region length (e.g., 3 groups based on same, longer, or shorter length of framework region). The group with the same length of framework region as the donor sequence is assigned a higher rank than the groups with longer or shorter length of framework region. The aligned framework and CDR residues between the non-human donor immunoglobulin and the selected germline sequence are then included in the back-mutation evaluation described below or used for acceptor framework ranking. For the group of germline sequence with longer or shorter framework regions, the insertion or deletion residue(s) is annotated and omitted from later back mutation evaluations. Insertion or deletions in the CDR region are also annotated and omitted from the strcdr evaluation.

In certain embodiments, the collection of potential acceptor sequences represent only partial acceptor frameworks (e.g., FR1–CDR1–FR2–CDR2–FR3–CDR3–XXX) and a complete acceptor framework must be assembled uysing additional human germline FR4 sequences. Unique human germline FR4 sequences from Vbase (http://vbase.mrc-cpe-.cam.ac.uk/) are summarized in Table 7. Human germline JH4 and JH5 have the same FR4 amino acid sequence as JH1 and are therefore excluded from the Table. Likewise, human germline JL2 and JL3 have the same FR4 amino acid sequence as JL2 and are excluded.

TABLE 7

Human germline FR4 sequence

| Region | Family | Other families | Sequence$^a$ | SEQ ID NO: |
|---|---|---|---|---|
| VH FR4 | JH1 | JH4, JH5 | WGQGTLVTVSS | 1 |
| | JH2 | | WGRGTLVTVSS | 2 |
| | JH3 | | WGQGTMVTVSS | 3 |
| | JH6 | | WGQGTTVTVSS | 4 |
| VL FR4 | JK1 | | FGQGTKVEIK | 5 |
| | JK2 | | FGQGTKLEIK | 6 |
| | JK3 | | FGPGTKVDIK | 7 |
| | JK4 | | FGGGTKVEIK | 8 |
| | JK5 | | FGQGTRLEIK | 9 |
| | JL1 | | FGTGTKVTVL | 14 |
| | JL2 | JL3 | FGGGTKLTVL | 15 |
| | JL7 | | FGGGTQLTVL | 16 |

$^a$Human germline FR4 sequences from Vbase

To select an appropriate FR4 sequence, the VL or VH FR4 sequence of the donor immunoglobulin is aligned against each of the corresponding human germline VL or VH FR4 sequences listed in Table 7, to identify the FR4 sequence with highest sequence identity. Sequence identity is defined as the total number of identical residues between the rodent FR4 and each human germline FR4. If only one human germline FR4 with the highest sequence identity to the donor FR4 is identified, this human germline FR4 will be selected as acceptor human FR4. If more than one human germline FR4 shows the highest sequence identity to the donor FR4, the residue similarity is then further checked for the non-identical residues between the donor FR4 and each human germline FR4, at step 220. Table 8 summarizes the chemical equivalency among different amino acid residues. For each non-identical position, the similarity score increases 1 if both amino acids are from the same chemical family.

TABLE 8

Amino acid chemical families

| Chemical Family | Amino Acid |
|---|---|
| Aliphatic | G, A, V, I, L |
| Aromatic | F, Y, W |
| Ionizable Basic | K, R, H |
| Acidic & Amides | E, D, N, Q |
| Hydroxyl | S, T |
| Sulfur-Containing | C, M |
| Cyclic | P |

The human germline FR4 with the highest sequence identity and the highest total similarity score is selected as acceptor human FR4. This sequence may then be appended to each of the partial acceptor sequences in the collection of potential acceptor sequences in order to generate complete acceptor sequences.

iii. Structural Analysis of the Donor Immunoglobulin (1) Providing a Structural Model At steps 152 and 207, in FIGS. 1B and 1C, respectively, structural analysis of the donor immunoglobulin is conducted to identify key framework residues in the donor framework regions that may be need to be retained if they are non-identical to those corresponding residue in the acceptor immuglobulin. These key residues may be identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved.

In certain exemplary embodiments, donor antibody structure is modeled using Antibody Modeler in Molecular Operating Environment (Molecular Operating Environment (MOE), 2011.10; Chemical Computing Group Inc., Montreal, QC, Canada). The MOE Antibody Homology Modeling accounts for the particular structural composition of antibodies when searching for template candidates and composing templates. As a result, models may be generated based on templates containing framework and CDR loops from different sources composed as dimers. In certain alternative embodiments, a knowledge-based approach may be applied with an underlying database of antibody structures currently in the Protein Data Bank (PDB), clustered by class, species, subclass and framework sequence identity. This database may be enriched with additional antibody structures and can be continually updated and reclustered.

In certain embodiments, multiple structural models can be provided for each donor antibody in order to generate a single consensus structure. The consensus structure is then used for further structure-based analysis. In other embodiments, structural models may be eliminated if they contain any deletion or gap in the modeled structure.

Having identified an appropriate structural model, one of ordinary skill in the art can annotate the modeled structure to identify CDRs or FRs by correlating the structure with the annotated sequence of the donor antibody provided above. For example, if there is a deletion or insertion at in the modeled structure, the structural model can be shifted or recalibrated to correlate with the structural positions of the original non-human donor antibody.

(2) Identifying Structurally Important Positions

At steps 153 and 208, in FIGS. 1B and 1C, respectively, the structural model of the donor antibody is examined to identify key framework region (FR) positions in the VH or VL where residues that occupy the positions are involved in the interaction with CDR residues or residues in the opposite chain of the VH/VL pair. Key structural FR positions may be classified according to one or more of the following structural criteria:

a. Strall (structure all) positions: FR residues which are within about 5 Å to one or more of the CDRs or VH/VL interface of the structural model. The choice of distance to CDRs can be adjusted if it is needed.

b. Buried positions: FR residues which are within 5 Å to CDRs or VH/VL interface of the immunoglobulin and whose solvent exposure percentage is less than 20%. Solvent exposure percentage of a particular residue may be calculated by dividing the solvent accessible surface area of the residue in the modeled structure by the solvent accessible surface area for the residue when it is in a linear GXG trimer, where X stand for the residue of interest.

c. Strltd (structure limited) positions: FR residues which interact with one or more CDRs of the structural model or another counterpart VH or VL chain of the model by specific hydrophobic, electrostatic, and ion-ion interactions. Hydrophobic, electrostatic, and ion-ion interactions are defined based on default distance cutoff used in MOE (insert number).

In other embodiments, the structural model of the donor antibody may also be examined to identify key CDR positions which interact with the key FR residues described above. For example, key CDR positions may be identified as follows:

d. Strcdr positions: CDR residues which interact with the strltd positions described above.

iv. Ranking and Selection of a Suitable Acceptor Framework

To select an suitable acceptor framework from the collection of all possible human germline VH or VL sequences with the same CDR canonical structures and Kabat subgroup assignment identified in step (ii)(2) above, all of the sequences in the collection are ranked according to the following scheme at steps 220-235, shown in FIG. 1C:

(1) identifying the number of non-identical residues at all framework region (FR) positions between the donor sequence and each acceptor sequence in the collection, at step 220;

(2) identifying the number of non-identical residues at key CDR positions ("strcdr") between the donor sequence and each acceptor sequence in the collection at step 225;

(3) ranking the acceptor sequences in the collection based on a preference score ("cliff") which is a sum of the number of non-identical residues identified in step (1) and (2) for each acceptor sequence, at step 230. Potential acceptor sequences may be ranked in ascending order.

(4) selecting the acceptor sequence in the collection with the lowest preference score, at step 235.

If more than one potential acceptor sequence shares the lowest preference score, only one of the potential acceptor sequences is chosen as the acceptor framework sequence. Alternatively, if VK1-O12 is among the group of potential human germline VL sequences with the lowest preference score, than VK1-O12 is selected as the acceptor.

In certain embodiments, the selection scheme may further comprise selecting the acceptor sequence in the collection with the lowest preference score and the lowest backmutation score ("fr_bm"). At step 175 (FIG. 1B), the acceptor sequence with the lowest backmutation score may be established by (5) identifying all key FR residues in the VL or VH sequence of the non-human donor immunoglobulin which are (a) within about 5 Angstroms of the CDRs of the VH/VL interface of the immunoglobulin and have a solvent exposure of less than 20% ("buried"); or (b) involved in the interaction with the CDR or another chain by specific hydrophobic, electrostatic or ion-ion chain interactions ("strltd"); and (6) for each acceptor sequence in the collection, identifying the number of non-identical residues at the key FR positions of step (5) between the donor sequence and each acceptor sequence to establish a total backmutation score ("fr_bm") for each acceptor sequence; and (7) ranking the acceptor sequences in the collection based on the backmutation score.

In yet other embodiments, the selection scheme may further comprise selecting the acceptor sequence in the collection with the with the lowest avoided backmutation ("avoid_bm") score. The acceptor sequence with the lowest avoided backmutation score may be established by (8) identifying the non-identical FR residues at all framework region (FR) positions between the donor sequence and each acceptor sequence in the collection;

(9) identifying the non-identical residues at the key FR positions of step (5) between the donor sequence and each acceptor sequence in the collection;

(10) identifying the number of non-identical FR residues from step (8) and (9) that are listed in Table 9 below to establish an avoided backmutation score for each acceptor sequence;

(11) ranking the acceptor sequences in the collection based on the avoided backmutation score; and

(12) identifying the acceptor sequence in the collection with the lowest avoided backmutation score.

TABLE 9

Avoided back-mutation sites (in Kabat numbering)

| | |
|---|---|
| VH | 2, 4, 24, 36, 37, 39, 43, 45, 49, 58, 60, 67, 68, 69, 70, 73, 74, 75, 76, 78, 91, 92, 93, 103 |
| VL | 4, 35, 36, 38, 43, 44, 46, 58, 62, 63, 64, 65, 66, 67, 68, 69, 70, 71, 73, 85, 87, 98 |

In still other embodiments, the selection scheme may further comprise assigning selecting the acceptor sequence based on its germline subfamily classification. For example, the acceptors in the collection may be ranked based on germline subfamily classification and the chosen acceptor is selected as the acceptor having the highest score in a desired germline subfamily. By way of example, the human VH germline sequences can be assigned to Kabat germline subgroups (e.g., VH1, VH2, VH3, VH4, VH5, VH6 or VH7) and ranked according to the criteria set forth above. If an acceptor sequence of the VH3 Kabat subfamily is desired, the VH3 germline with the lowest ranking score may then be selected for as the chosen acceptor. Alternatively, if an acceptor sequence of the VH1 Kabat subfamily is desired, the VK1 germline with the lowest ranking score may then be selected for as the chosen acceptor.

iv. Backmutation Evaluation

Having selected a suitable human acceptor framework according to the criteria outlined in step (iii) above, a humanized design is synthesized at step 180 (FIG. 1B) which incorporates the CDRs of the non-human donor immunoglobulin together with a limited set of framework region (FR) backmutations at key FR positions where the amino acids in the chosen acceptor frameworks are non-identical to the amino acids occupying corresponding positions in the non-human donor immunoglobulins. Preferably, these backmutations restore or improve, any loss in antigen binding affinity due to grafting of the donor CDRs in the acceptor framework.

Appropriate framework substitutions may be identified by methods well known in the art, e.g., by modeling of the interactions of the CDR and framework residues to identify framework residues important for antigen binding and sequence comparison and to identify unusual framework residues at particular positions. (See, e.g., Queen et al., U.S. Pat. No. 5,585,089; Riechmann et al., Nature 332:323 (1988), which are incorporated herein by reference in their entireties). These key residues may be selected from the group consisting of:
- a residue adjacent to a CDR;
- a glycosylation site residue;
- a rare residue;
- a residue capable of interacting with antigen;
- a residue capable of interacting with a CDR;
- a canonical residue;
- a contact residue between heavy chain variable region and light chain variable region;
- a residue within a Vernier zone; and
- a residue in a region that overlaps between a Chothia-defined variable heavy chain CDR1 and a Kabat-defined first heavy chain framework.

In one exemplary embodiment, the key FR amino acids from the donor immunoglobulin that replace the non-identical amino acids at corresponding FR positions in the selected acceptor variable region framework are identified by:

(1) providing a structural model of the non-human donor immunoglobulin sequence;

(2) identifying all key FR residues (v1="strall"+"strltd") in the VL or VH sequence of the non-human donor immunoglobulin which are (a) within about 5 Angstroms of the CDRs or VH/VL interface of the donor immunoglobulin sequence ("strall") or (b) involved in the interaction with the CDR or another chain by specific hydrophobic, electrostatic or ion-ion chain interactions ("strltd");

(3) comparing the key FR residues of step (xxi) with the residues present at corresponding amino acid positions in the selected acceptor variable region framework to identify all key FR residues that are non-identical.

In one exemplary embodiment, the key FR amino acids from the donor immunoglobulin that replace the non-identical amino acids at corresponding FR positions in the selected acceptor variable region framework are identified by:

(1) providing a structural model of the non-human donor immunoglobulin sequence;
(2) identifying all key FR residues (v2="buried"+"strltd") in the VL or VH sequence of the non-human donor immunoglobulin which are (a) within about 5 Angstroms of the CDRs or VH/VL interface of the immunoglobulin and have a solvent exposure of less than 20% ("buried") or (b) involved in the interaction with the CDR or another chain by specific hydrophobic, electrostatic or ion-ion chain interactions ("strltd");
(3) comparing the key FR residues of step (xxi) with the residues present at corresponding amino acid positions in the selected acceptor variable region framework to identify all key FR residues that are non-identical.

In yet another embodiment, the key FR amino acids from the donor immunoglobulin that replace the non-identical amino acids at corresponding FR positions in the selected acceptor variable region framework are identified by:
(1) providing a structural model of the non-human donor immunoglobulin sequence;
(2) identifying all key FR residues (v3="strltd") in the VL or VH sequence of the non-human donor immunoglobulin which are involved in the interaction with the CDR or another chain by specific hydrophobic, electrostatic or ion-ion chain interactions ("strltd");
(3) comparing the key FR residues of step (xxi) with the residues present at corresponding amino acid positions in the selected acceptor variable region framework to identify all key FR residues that are non-identical.

In certain embodiments, the humanized variant that is selected for synthesis is the humanized sequence with the lowest "sequence liability" score. "Liability scoring" is conducted by analyzing the sequence for the presence of certain sequence motifs that are prone to unwanted post-translational modification. For example, a particular humanized variant variant can be assigned a higher score for each sequence motif that poses a high risk for deamidation (e.g., NG, NS, QG), isomerization (e.g., DG, DS, DH), cleavage (e.g, DP), oxidation (e.g., M or C), glycosylation (e.g., N(P)S or N(P)T). Residues that pose are moderate (e.g., NP or TS) or low risk (e.g., SN, TN, KN, NN or N-terminal pyroglutamate) may be assigned a lower score. The humanized variant that is selected for synthesis has the lowest total liability score.

C. Production of Humanized Antibodies

Humanized antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

D. Humanized Antibodies

Preferably, the humanized antibodies of the present invention, exhibit substantially similar biological activity, e.g., target binding affinity, as the parental non-human antibodies from which they are derived, e.g., as assessed by any one of several in vitro and in vivo assays known in the art. In certain preferred embodiments, the engineered antibody exhibits improved activity with respect to its corresponding parental antibody. For example, the engineered antibody may dissociate from its target antigen with a $k_{off}$ rate constant of about 0.1 s$^{-1}$ or less, as determined by surface plasmon resonance, or inhibit the activity of the target antigen with an IC$_{50}$ of about 1×10$^{-6}$M or less. Alternatively, the antibody, or an antigen-binding portion thereof, may dissociate from the target antigen with a $k_{off}$ rate constant of about $1\times10^{-2}$ s$^{-1}$ or less, as determined by surface plasmon resonance, or may inhibit activity of the target antigen with an IC$_{50}$ of about $1\times10^{-7}$M or less. Alternatively, the antibody, or an antigen-binding portion thereof, may dissociate from the target with a $k_{off}$ rate constant of about $1\times10^{-3}$ s$^{-1}$ or less, as determined by surface plasmon resonance, or may inhibit the target with an IC$_{50}$ of about $1\times10^{-8}$M or less. Alternatively, the antibody, or an antigen-binding portion thereof, may dissociate from the target with a $k_{off}$ rate constant of about $1\times10^{-4}$ s$^{-1}$ or less, as determined by surface plasmon resonance, or may inhibit its activity with an IC$_{50}$ of about $1\times10^{-9}$M or less. Alternatively, the antibody, or an antigen-binding portion thereof, may dissociate from the target with a $k_{off}$ rate constant of about $1\times10^{-5}$ s$^{-1}$ or less, as determined by surface plasmon resonance, or inhibit its activity with an IC$_{50}$ of about $1\times10^{-10}$M or less. Alternatively, the antibody, or an antigen-binding portion thereof, may dissociate from the target with a $k_{off}$ rate constant of about $1\times10^{-5}$ s$^{-1}$ or less, as determined by surface plasmon resonance, or may inhibit its activity with an IC$_{50}$ of about $1\times10^{-11}$M or less.

In certain embodiments, the humanized antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the humanized antibody comprises an engineered Fc region. Replacements of amino acid residues in the Fc portion to alter antibody effector function are known in the art (see, e.g., Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

In certain embodiments, the humanized antibody is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

In other embodiment, the humanized binding protein is further modified to generate glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

In still another embodiment, the glycosylation of the engineered antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a humanized antibody of the invention can be further modified with an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Sequence Analysis of 10B3 Donor Antibody

Rodent antibody 10B3 was used as an exemplary donor immunoglobulin to illustrate the computer-aided automation of humanization designs. The 10B3 variable region heavy chain sequence is saved in file "10B3_vh.fasta" in following format:

>10B3_VH
EVKLVESGGGLVQPGGSRKLSCAASGFTFSDYEM-VWVRQAPGEGLEWVAY ISSGSRTIHYADTVK-GRFTISRDNPKNTLFLQMSSLRSEDTAMYY-CARTLLRL HFDYWGQGTILTVSS (SEQ ID NO: 17)

The antibody sequence was further annotated into segment files named as 0B3_vh.fasta.segments as follows:

10B3_VH
  fr1 EVKLVESGGGLVQPGGSRKLSCAAS (SEQ ID NO: 18)
  fr2 WVRQAPGEGLEWVA (SEQ ID NO: 19)
  fr3 RFTISRDNPKNTLFLQMSSLRSEDTAMYYCAR (SEQ ID NO: 20)
  fr4 WGQGTILTVSS (SEQ ID NO: 21)
  cdr1 gftfsdyemv (SEQ ID NO: 22)
  cdr2 yissgsrtihyadtvkg (SEQ ID NO: 23)
  cdr3 tllrlhfdy (SEQ ID NO: 24)

Based on the annotated segment files, 10B3_vh.fasta.segments were renumbered with Kabat numbering by creating a file "10B3_vh_kabat" which coverts position number (first column) and Kabat number (second column) for each residue in 10B3_vh (SEQ ID NO: 17):

| | | |
|---|---|---|
| 1 | 1 | E |
| 2 | 2 | V |
| 3 | 3 | K |
| 4 | 4 | L |
| 5 | 5 | V |
| 6 | 6 | E |
| 7 | 7 | S |
| 8 | 8 | G |
| 9 | 9 | G |
| 10 | 10 | G |
| 11 | 11 | L |
| 12 | 12 | V |
| 13 | 13 | Q |
| 14 | 14 | P |
| 15 | 15 | G |
| 16 | 16 | G |
| 17 | 17 | S |
| 18 | 18 | R |
| 19 | 19 | K |
| 20 | 20 | L |
| 21 | 21 | S |
| 22 | 22 | C |
| 23 | 23 | A |
| 24 | 24 | A |
| 25 | 25 | S |
| 26 | 26 | g |
| 27 | 27 | f |
| 28 | 28 | t |
| 29 | 29 | f |
| 30 | 30 | s |
| 31 | 31 | d |
| 32 | 32 | y |
| 33 | 33 | e |
| 34 | 34 | m |
| 35 | 35 | v |
| 36 | 36 | W |
| 37 | 37 | V |
| 38 | 38 | R |
| 39 | 39 | Q |
| 40 | 40 | A |
| 41 | 41 | P |
| 42 | 42 | G |
| 43 | 43 | E |
| 44 | 44 | G |
| 45 | 45 | L |
| 46 | 46 | E |
| 47 | 47 | W |
| 48 | 48 | V |
| 49 | 49 | A |
| 50 | 50 | y |
| 51 | 51 | i |
| 52 | 52 | s |
| 53 | 52a | s |
| 54 | 53 | g |
| 55 | 54 | s |
| 56 | 55 | r |
| 57 | 56 | t |
| 58 | 57 | i |
| 59 | 58 | h |
| 60 | 59 | y |
| 61 | 60 | a |
| 62 | 61 | d |
| 63 | 62 | t |
| 64 | 63 | v |
| 65 | 64 | k |
| 66 | 65 | g |
| 67 | 66 | R |
| 68 | 67 | F |
| 69 | 68 | T |
| 70 | 69 | I |
| 71 | 70 | S |
| 72 | 71 | R |
| 73 | 72 | D |
| 74 | 73 | N |
| 75 | 74 | P |
| 76 | 75 | K |
| 77 | 76 | N |
| 78 | 77 | T |
| 79 | 78 | L |
| 80 | 79 | F |
| 81 | 80 | L |
| 82 | 81 | Q |
| 83 | 82 | M |
| 84 | 82a | S |
| 85 | 82b | S |
| 86 | 82c | L |
| 87 | 83 | R |
| 88 | 84 | S |
| 89 | 85 | E |
| 90 | 86 | D |
| 91 | 87 | T |
| 92 | 88 | A |
| 93 | 89 | M |
| 94 | 90 | Y |
| 95 | 91 | Y |
| 96 | 92 | C |
| 97 | 93 | A |
| 98 | 94 | R |
| 99 | 95 | t |

-continued

| | | |
|---|---|---|
| 100 | 96 | l |
| 101 | 97 | l |
| 102 | 98 | r |
| 103 | 99 | l |
| 104 | 100 | h |
| 105 | 100a | f |
| 106 | 101 | d |
| 107 | 102 | y |
| 108 | 103 | W |
| 109 | 104 | G |
| 110 | 105 | Q |
| 111 | 106 | G |
| 112 | 107 | T |
| 113 | 108 | I |
| 114 | 109 | L |
| 115 | 110 | T |
| 116 | 111 | V |
| 117 | 112 | S |
| 118 | 113 | S |

In the rodent antibody 10B3 heavy chain variable domain, insertions occur in CDR2, CDR3 and FR3 as highlighted by red circle in FIG. 2. Based on the length of heavy chain CDR1 (10), CDR2 (17), the amino acid types at Kabat positions 54 (S) and 71 (R), the CDR canonical structure for 10B3 heavy chain variable domain was assigned as vh.1-3. This means that heavy chain CDR1 has canonical structure 1 and CDR2 has canonical structure 3 as defined in Table 2 above.

Example 2

Compiling a Collection of Acceptor Framework (FR) Sequences for 10B3 Donor Antibody A human germline database was established comprising the 61 unique VH germline sequences from Table 3, 36 unique VKappa germline sequences from Table 4, and 31 unique VLambda germline sequences from Table 5. Table 3 includes 49 unique VH germline sequences from Vbase (http://vbase.mrc-cpe.cam.ac.uk/) and 12 additional unique VH germline sequence from NCBI (http://www.ncbi.nlm.nih.gov/). Table 4 includes 32 unique VKappa germline sequences from Vbase (http://vbase.mrc-cpe.cam.ac.uk/) and 4 additional unique VKappa germline sequences from NCBI (http://www.ncbi.nlm.nih.gov/).

The CDR canonical structure of each germline sequence in the database was assigned. Human germline sequences are clustered into sub-groups according to their CDR canonical structures as shown in Table 6.

To identify a potential acceptor sequence, only the human germline amino acid sequences in the subgroup with the same CDR canonical structure as the rodent antibody were further considered. As discussed above, rodent antibody 10B3 heavy chain has canonical structural vh.1-3. The acceptor human framework search was therefore carried with the collection of 26 human germline database named vh.1-3 and depicted in FIG. 3.

In addition, to identify an acceptor FR4 sequence, the donor VH FR4 sequence was aligned against human germline VH FR4 sequences listed in Table 7 as shown in FIG. 4. JH3, JH6 and JH1 show the same sequence identity (81.8%) to 10B3 VH FR4. However, according to Table 8, JH1 has the highest sequence similarity to 10B3 VH FR4. Accordingly, JH1 was selected as the acceptor FR4 and appended to each the FR1-FR3 sequences in the collection.

Example 3

Structural Analysis of the 10B3 Donor Antibody

A consensus structure was generated for the donor antibody sequence in order to facilitate further structure-based analysis. Based on the modeled 10B3 structure showed in FIG. 5, buried (FR buried residues and 5 Å around CDRs), strltd (FR residues interacting with CDR or VL) and strcdr (CDR residues interacting with FR residue) positions were identified for 10B3 VH. Those positions are highlighted based on 10B3 VH sequence in cyan, yellow, and purple in FIG. 6.

Example 4

Ranking Acceptor Frameworks for Selection of a Suitable Acceptor

To rank all potential acceptor human frameworks identified in Example 2, a diff score; "fr-bm" score" and "avoid-bm" score was calculated for each acceptor human germline in the collection. Potential acceptor human FRs are ranked for each score in ascending order (see FIG. 7). Since VH3-48 had the lowest diff score, it was selected as acceptor human framework for the 10B3 VH sequence.

Example 5

Synthesis of Humanized 10B3 Variants with the Selected Acceptor

Having selected a suitable receptor the HCDRs of the donor 10B3 VH sequence were grafted into the framework of the selected acceptor sequence (VH3-48). Important structural positions requiring backmutation were identified (see FIG. 8 depicts back mutation sites highlighted in green).

A total of 3 humanized variants were constructed: 10B3_VH3-48_v1; 10B3_VH3-48_v2; and 10B3_VH3-48_v3.

"v1" contains backmutations at Q3K, S49A, A75P, S78T and Y80F.
>10B3_VH3-48_v1
evKlvesggglvqpggslrlscaasgftfsdyemvwvrqapgkglewv AyissgsrtihyadtvkgrftisrdnPknTlFlqmnslr dedtavyycartllrl-hfdywgqgtivtvss (SEQ ID NO: 25)

"v2" contains backmutations at S49A, S78T and Y80F.
>10B3_VH3-48_v2
evqlvesggglvqpggslrlscaasgftfsdyemvwvrqapgkglewv AyissgsrtihyadtvkgrftisrdnaknTlFlqmnslrd edtavyycartllrl-hfdywgqgtivtvss (SEQ ID NO: 26)

"v3" contains no backmutations.
>10B3_VH3-48_v3
evqlvesggglvqpggslrlscaasgftfsdyemvwvrqapgkglew-vsyissgsrtihyadtvkgrftisrdnaknslylqmnslide dtavyycartllrl-hfdywgqgtivtvss (SEQ ID NO: 27)

Example 6

Exemplary Software for Computer Implementation of Humanization Design

The following Python, Pert and shell scripts 125 are included in the current automated humanization design. Each of the scripts invokes a corresponding algorithm 124 (which may be stored in database 122):
a. analysis_seq.py for rodent antibody sequence analysis calls for the following programs:

i. annotate_seq.pl for annotating CDR and FR in antibody sequence
ii. search_db.pl for human germline database search
iii. seqidentity.pl for sequence identity calculation
iv. HMM for sequence alignment called by annotate_seq.pl and search_db.pl b. analysis_str.py for rodent antibody structure analysis calls following programs:
 i. MOE for antibody structure modeling
 ii. protein_batchfile.svl for structure-based property calculation
 iii. fab_contacts.svl for antibody contacts calculation c. back_mutation.py for back-mutation evaluation humanization.sh for streamlining the design process and generating final report (section 4.4) calls following program:
 i. ientify_VLtm.py for preferring VK1-012 when it is in the top ranking group.

Example 7

Computer Implemented Humanization of Additional Rodent Antibodies

Three additional rodent antibodies (mAb1, mAb2, and mAb3) were humanized using the high-throughput antibody humanization program.

A. Design Detail of mAb1:

For mAb1, VH and VL sequences were annotated into segments and numbered with Kabat numbering. mAb1 VH CDR was identified as having the canonical structure 1-3, while the VLCDR was identified as having the canonical structure, 2-1-1. Accordingly, an acceptor human framework search for FR1-FR3 of the heavy chain was carried with a collection of 26 human germlines in a database named vh.1-3. An acceptor human framework search for FR1-FR3 of the light chain was carried out with human germline database named vk.2-1-1. JH6 was selected as the acceptor FR4 for mAb1 VH and JK2 was selected as the acceptor FR4 for mAb1 VL.

A consensus structure was then generated for mAb1. Based on the modeled mAb1 the buried, strltd, strcdr residues for the VH domain of mAb1 were identified as follows: "buried_vh" [Kabat positions 4, 22, 24, 25, 36, 37, 38, 39, 44, 45, 47, 48, 49, 66, 67, 68, 69, 71, 77, 78, 80, 86, 90, 91, 92, 93 and 94], "strltd_vh" [Kabat positions 4, 37, 39, 45, 47, 48, 66, 67, 69, 71, 73 and 78], and "strcdr_vh" [Kabat positions 29, 34, 35, 51, 52, 57, 59, 63, 64, 95, 98, 100d and 101], where "buried_vh" are VH FR residues within 5 Angstrom to CDRs or VL with solvent exposure percentage of <20%, "strltd_vh" are VH FR residues whose sidechains interact with CDRs or VL, and "strcdr_vh" are VH CDR residues whose sidechains interact with residues in strltd_vh and/or strltd_vl.

Based on the ranking of all possible acceptor human VH germlines (see Table 9), IGHV3-48*01 was identified as the best human acceptor framework sequence for mAb1 VH. A total of three (3) humanized variants were designed for mAb1 VH, having 0, 3 (V37I, S49A, S77T, Kabat Numbering) and 1 (V37I) framework back-mutations, respectively. The mAb1 VH design with 3 back-mutations was selected for further experimentation.

TABLE 9

Acceptor Human VH Germline Ranking For mAb1

| germline | diff | fr_bm | avoid_bm |
| --- | --- | --- | --- |
| IGHV3-48*01 | 12 | 3 | 2 |
| IGHV3-48*02 | 12 | 3 | 2 |
| IGHV3-30*03 | 13 | 1 | 1 |
| IGHV3-21*01 | 13 | 3 | 2 |
| IGHV3-11*01 | 14 | 2 | 1 |
| IGHV3-30*18 | 14 | 2 | 1 |
| IGHV3-7*01 | 14 | 2 | 1 |
| IGHV3-74*01 | 15 | 2 | 2 |
| IGHV3-23*01 | 16 | 3 | 2 |
| IGHV3-64*01 | 16 | 3 | 2 |
| IGHV3-43*01 | 16 | 4 | 2 |
| IGHV3-20*01 | 16 | 4 | 3 |
| IGHV3-64*02 | 17 | 3 | 2 |
| IGHV3-35*01 | 19 | 5 | 4 |
| IGHV3-16*01 | 23 | 6 | 5 |
| IGHV1-3*01 | 33 | 8 | 6 |
| IGHV1-46*01 | 33 | 8 | 6 |
| IGHV1-2*02 | 35 | 8 | 6 |
| IGHV1-3*02 | 35 | 8 | 6 |
| IGHV1-45*01 | 36 | 8 | 6 |
| IGHV1-58*02 | 36 | 9 | 6 |
| IGHV1-58*01 | 37 | 9 | 6 |
| IGHV1-24*01 | 37 | 11 | 7 |

Based on the modeled mAb1 the buried, strltd, strcdr residues for the VL domain of mAb1 were identified as follows: buried_vl [2, 4, 6, 22, 23, 35, 36, 38, 43, 44, 46, 47, 48, 49, 57, 58, 59, 62, 64, 71, 87 and 88 (Kabat numbering)], strltd_vl [2, 4, 36, 38, 45, 46, 48 and 49 (Kabat numbering)], and strcdr_vl [29, 32, 33, 34, 50, 52, 53, 54, 55, 89, 92, 96], where "buried_vl" are VL FR residues within 5 Angstrom to CDRs or VH with solvent exposure percentage <20%, "strltd_vl" are VL FR residues whose sidechains interact with CDRs or VH, and "strcdr_vl" are VL CDR residues whose sidechains interact with residues in strltd_vh and/or strltd_vl.

Based on the ranking of all possible acceptor human VL germlines (see Table 10), IGKV1-16*01 is identified as the best human acceptor framework sequence for mAb1 VL. A total of three (3) humanized variants were designed for mAb1 VH, having 0, 3 (V37I, S49A, S77T, Kabat Numbering) and 1 (V37I) framework back-mutations, respectively. A total of three (3) humanized variants were designed for mAb1 VL, having 0, 6 (T22A, A43S, K45R, S46R, F71Y, Y87H) and 2 (K45R, S46R) framework back-mutations, respectively. The mAb1 VL design with 2 back-mutations was selected for further experimentation.

TABLE 10

Acceptor Human VL Germline Ranking For mAb1

| germline | diff | fr_bm | avoid_bm |
| --- | --- | --- | --- |
| IGKV1-16*01 | 20 | 6 | 4 |
| IGKV1-27*01 | 20 | 7 | 5 |
| IGKV1-17*01 | 21 | 6 | 4 |
| IGKV1-33*01 | 21 | 7 | 5 |
| IGKV1-39*01 | 21 | 7 | 5 |
| IGKV1-12*01 | 22 | 7 | 5 |
| IGKV1-6*01 | 22 | 7 | 5 |
| IGKV1D-16*01 | 22 | 7 | 5 |
| IGKV1-13*01 | 22 | 8 | 6 |
| IGKV1-37*01 | 22 | 8 | 6 |
| IGKV1-5*01 | 23 | 7 | 5 |
| IGKV1-8*01 | 23 | 7 | 5 |
| IGKV1D-17*01 | 24 | 6 | 4 |
| IGKV1-9*01 | 24 | 8 | 6 |
| IGKV1D-43*01 | 25 | 7 | 4 |

TABLE 10-continued

Acceptor Human VL Germline Ranking For mAb1

| germline | diff | fr_bm | avoid_bm |
|---|---|---|---|
| IGKV1D-42*01 | 29 | 9 | 4 |
| IGKV3-15*01 | 33 | 7 | 6 |
| IGKV3-11*01 | 33 | 8 | 7 |
| IGKV6D-41*01 | 33 | 9 | 5 |
| IGKV3D-11*01 | 34 | 8 | 7 |
| IGKV6-21*01 | 35 | 8 | 5 |
| IGKV5-2*01 | 39 | 13 | 8 |

Finally, sequence liability screening was carried out on the final humanization design. The following residues were identified as having liabilities:

VH potential high risk deamidation framework residue [76-NS, 82a-NS, 105-QG]

VH potential high risk oxidation framework residue [82-M]

VH potential high risk oxidation CDR residue [34-M, 100d-M]

VH potential low risk deamidation framework residue [75-KN]

VH potential low risk deamidation CDR residue [30-SN, 55-SN]

VL potential high risk deamidation framework residue [100-QG]

VL potential high risk isomerization CDR residue [56-DG]

VL potential high risk oxidation framework residue [4-M]

B. Design Detail of mAb2:

For mAb2, VH and VL sequences were annotated into segments and numbered with Kabat numbering. mAb2 VH CDR was identified as having the canonical structure 2-1, while the VLCDR was identified as having the canonical structure, 2-1-1. Accordingly, an acceptor human framework search for FR1-FR3 of the heavy chain was carried with a collection of human germlines in a database named vh.2-1. An acceptor human framework search for FR1-FR3 of the light chain was carried out with human germline database named vk.2-1-1. JH1 was selected as the acceptor FR4 for mAb2 VH and JK2 was selected as the acceptor FR4 for mAb2 VL.

A consensus structure was generated for mAb2. Based on the modeled mAb2 the buried, strltd, strcdr for mAb2 VH were identified: "buried_vh" [2, 4, 24, 25, 36, 37, 38, 39, 40, 45, 46, 47, 48, 49, 66, 67, 68, 69, 76, 77, 78, 79, 80, 82, 86, 91, 92, 93, 94], "strltd_vh"[4, 24, 37, 45, 47, 48, 67, 69, 76, 78], and "strcdr_vh" [29, 35, 51, 52, 57, 60, 63, 95, 98, 100b, 100c].

Based on the ranking of all possible acceptor human VH germlines (see Table 11), IGHV4-28*01 was identified as the best human acceptor framework sequence for mAb2 VH. A total of three (3) humanized variants were designed for mAb2 VH, having 0, 10 (V2I, S25T, Q39K, P40F, L45M, I48M, V67I, T68S, M69I, S79F.) and 4 (L45M, I48M, V67I, M69I) framework back-mutations, respectively. The mAb2 VH design with 4 back-mutations was tested in experiment.

TABLE 11

Acceptor Human VH Germline Ranking For mAb2

| germline | diff | fr_bm | avoid_bm |
|---|---|---|---|
| IGHV4-28*01 | 26 | 10 | 6 |
| IGHV4-4*02 | 27 | 10 | 6 |

Based on the modeled mAb2, the following buried, strltd, and strcdr residues for mAb2 VL were identified (Kabat numbering): "buried_vl" [2, 4, 6, 22, 23, 35, 36, 38, 43, 44, 46, 47, 48, 49, 57, 58, 59, 61, 62, 64, 68, 71, 85, 87, 88], "strltd_vl" [2, 4, 36, 46, 48, 58, 62, 70, 71], and "strcdr_vl" [24, 26, 29, 32, 33, 54, 89, 90, 92, 97].

Based on the ranking of all possible acceptor human VL germlines (see Table 12), IGKV3-11*01 is identified as the best human acceptor framework sequence for mAb2 VL. A total of three (3) humanized variants were designed for mAb2 VH, having 0, 5 (I2T, A43Q, I58V, V85T, Y87F) and 2 (I2T, I58V) framework back-mutations, respectively. The mAb2 VL design with 2 back-mutations was selected for further testing.

TABLE 12

Acceptor Human VL Germline Ranking For mAb2

| germline | diff | fr_bm | avoid_bm |
|---|---|---|---|
| IGKV3-11*01 | 21 | 5 | 4 |
| IGKV3D-11*01 | 22 | 5 | 4 |
| IGKV3-15*01 | 23 | 7 | 6 |
| IGKV6D-41*01 | 25 | 6 | 3 |
| IGKV1-13*01 | 26 | 4 | 2 |
| IGKV1-37*01 | 26 | 4 | 2 |
| IGKV6-21*01 | 26 | 5 | 2 |
| IGKV1-27*01 | 26 | 5 | 3 |
| IGKV1-39*01 | 26 | 5 | 3 |
| IGKV1-9*01 | 26 | 5 | 3 |
| IGKV1-5*01 | 26 | 6 | 4 |
| IGKV1-12*01 | 27 | 5 | 3 |
| IGKV1-6*01 | 27 | 5 | 3 |
| IGKV1-33*01 | 28 | 5 | 3 |
| IGKV1-8*01 | 28 | 5 | 3 |
| IGKV1D-16*01 | 28 | 6 | 4 |
| IGKV1-16*01 | 28 | 7 | 5 |
| IGKV1-17*01 | 28 | 7 | 5 |
| IGKV1D-43*01 | 31 | 7 | 4 |
| IGKV5-2*01 | 31 | 7 | 5 |
| IGKV1D-17*01 | 31 | 8 | 6 |
| IGKV1D-42*01 | 33 | 9 | 4 |

Finally, sequence liability screening was carried out on the final humanization design. The following residues were identified as having liabilities:

VH potential high risk oxidation framework residue [45-M, 48-M]

VH potential medium risk hydrolysis CDR residue [60-NP]

VH potential medium risk cleavage framework residue [73-TS]

VH potential medium risk cleavage CDR residue [30-TS]

VH potential low risk deamidation framework residue [75-KN]

VL potential high risk deamidation framework residue [100-QG]

VL potential high risk isomerization CDR residue [55-DS]

VL potential high risk cleavage CDR residue [94-DP]

VL potential low risk deamidation CDR residue [52-SN]

C. Design Detail of mAb3:

For mAb3, VH and VL sequences were annotated into segments and numbered with Kabat numbering. mAb3 VH CDR was identified as having the canonical structure 1-2 and mAb 3 VL CDR was identified as having the canonical structure 2-1-1. The acceptor human framework search for FR1-FR3 of the VH was carried with human germline database named vh.1-2, while the acceptor human framework search for FR1-FR3 of VL was carried with human germline database named vk.2-1-1. JH3 was selected as the acceptor FR4 for mAb3 VH. JK2 was selected as the acceptor FR4 for mAb3 VL.

A consensus structure was generated for mAb3. Based on the modeled mAb3 the buried, strltd, strcdr for mAb3 VH were identified (Kabat numbering): "buried_vh" [2, 4, 22, 23, 24, 25, 36, 37, 38, 39, 44, 45, 47, 48, 49, 66, 67, 68, 69, 71, 77, 78, 79, 90, 91, 92, 93, 94], "strltd_vh" [4, 37, 39, 45, 48, 67, 69, 71, 94] and "strcdr_vh" [29, 34, 51, 52a, 53, 59, 63, 64, 95, 99, 100d, 100f, 101, 102].

Based on the ranking of all possible acceptor human VH germlines (see Table 13), IGHV7-4-1*01 is identified as the best human acceptor framework sequence for mAb3 VH. A total of two (2) humanized variants were designed for mAb3 VH, having 0 or 4 (V2I, R38K, W47Y, Y91F) framework back-mutations, respectively. The mAb3 VH design with 0 back-mutations was selected for further testing.

TABLE 13

Acceptor Human VH Germline Ranking For mAb3

| germline | diff | fr_bm | avoid_bm |
|---|---|---|---|
| IGHV7-4-1*01(0-1) | 18 | 4 | 2 |
| IGHV7-81*01 | 20 | 5 | 2 |
| IGHV1-69*01 | 30 | 8 | 5 |
| IGHV1-69*06 | 30 | 8 | 5 |
| IGHV1-18*01 | 31 | 8 | 5 |
| IGHV5-51*01 | 32 | 10 | 6 |
| IGHV1-f*01(0-1) | 33 | 10 | 6 |
| IGHV5-a*01(0-1) | 33 | 10 | 6 |

Based on the modeled mAb3 the buried, strltd, strcdr for mAb3 VL were identified (Kabat numbering): "buried_vl" [2, 4, 6, 22, 23, 35, 36, 38, 44, 46, 47, 48, 49, 57, 58, 59, 61, 62, 64, 71, 85, 87, 88]; "strltd_vl" [2, 4, 38, 48, 70, 71, 87], and "strcdr_vl" [24, 26, 27, 29, 33, 34, 54, 90, 91, 96].

Based on the ranking of all possible acceptor human VL germlines (see Table 14), IGKV3-11*01 was identified as the best human acceptor framework sequence for mAb3 VL. A total of three (3) humanized variants were designed for mAb3 VH, 0, 4 (12T, 158V, V85T, Y87F) and 2 (12T, Y87F) framework back-mutations, respectively. The mAb3 VH design with 4 back-mutations was selected for further testing.

TABLE 14

Acceptor Human VL Germline Ranking For mAb3

| germline | diff | fr_bm | avoid_bm |
|---|---|---|---|
| IGKV3-11*01 | 22 | 4 | 3 |
| IGKV3D-11*01 | 23 | 4 | 3 |
| IGKV6D-41*01 | 23 | 5 | 2 |
| IGKV6-21*01 | 24 | 4 | 1 |
| IGKV3-15*01 | 24 | 6 | 5 |
| IGKV1-13*01 | 25 | 3 | 1 |
| IGKV1-37*01 | 25 | 3 | 1 |
| IGKV1-27*01 | 25 | 4 | 2 |
| IGKV1-39*01 | 25 | 4 | 2 |
| IGKV1-9*01 | 25 | 4 | 2 |
| IGKV1-5*01 | 25 | 5 | 3 |
| IGKV1-12*01 | 26 | 4 | 2 |

TABLE 14-continued

Acceptor Human VL Germline Ranking For mAb3

| germline | diff | fr_bm | avoid_bm |
|---|---|---|---|
| IGKV1-6*01 | 26 | 4 | 2 |
| IGKV1-33*01 | 27 | 4 | 2 |
| IGKV1-8*01 | 27 | 4 | 2 |
| IGKV1D-16*01 | 27 | 5 | 3 |
| IGKV1-16*01 | 27 | 6 | 4 |
| IGKV1-17*01 | 27 | 6 | 4 |
| IGKV1D-43*01 | 30 | 6 | 3 |
| IGKV5-2*01 | 30 | 6 | 4 |
| IGKV1D-17*01 | 30 | 7 | 5 |
| IGKV1D-42*01 | 31 | 8 | 3 |

Finally, sequence liability screening was carried out on the final humanization design of mAb3. The following residues were identified as having liabilities:

VH potential high risk deamidation framework residue [43-QG, 105-QG]

VH potential high risk oxidation framework residue [48-M, 108-M]

VH potential high risk oxidation CDR residue [34-M]

VH potential medium risk cleavage framework residue [73-TS]

VH potential low risk deamidation CDR residue [30-TN, 95-TN]

VL potential high risk deamidation framework residue [101-QG]

VL potential high risk cleavage CDR residue [95-DP]

VL potential high risk oxidation CDR residue [24-C, 34-M, 89-C]

VL potential low risk deamidation CDR residue [53-SN]

D. Binding Affinity of Humanized Designs:

All 3 rodent antibodies (mAb1, mAb2, and mAb3) that were humanized using the high-throughput antibody humanization program, were synthesized and testing for binding to their cognate antigen using Biacore. As depicted in Table 15 below, all three humanized designed maintained the original binding affinities of the counterpart chimeric antibody containing the counterpart rodent variable domain. Accordingly, the computer-implemented design program can result in the production of successful humanized designs.

TABLE 15

Antigen Binding Affinity of Humanized Designs

| mAbs* | ka (M−1s−1) | Kd (s−1) | KD (M) |
|---|---|---|---|
| ch mAb1 | 8.60E+04 | 6.90E−05 | 8.00E−10 |
| hu mAb1 | 8.60E+04 | 1.80E−04 | 2.10E−09 |
| ch mAb2 | 7.50E+04 | 8.70E−05 | 1.20E−09 |
| hu mAb2 | 7.00E+04 | 1.50E−04 | 2.10E−09 |
| ch mAb3 | 1.20E+07 | 4.70E−05 | 3.80E−12 |
| hu mAb3 | 4.90E+06 | 3.60E−05 | 7.30E−12 |

We claim:

1. A method of producing a humanized variant of a non-human donor immunoglubin comprising the steps of:
   (i) providing a collection of all possible human immunoglobulin light chain variable region (VL) sequences or heavy chain variable region (VH) sequences with the same CDR canonical structures and Kabat subgroup assignment as the VL or VH sequence of the non-human donor immunoglobulin;
   (ii) for each acceptor sequence in the collection, identifying the number of non-identical residues at all framework region (FR) positions between the donor sequence and each acceptor sequence;
   (iii) for each acceptor sequence in the collection, identifying the number of non-identical residues at key CDR positions ("strcdr") between the donor sequence and each acceptor sequence;
   (iv) ranking the acceptor sequences in the collection based on a preference score ("diff") which is a sum of the number of non-identical residues identified in step (ii) and (iii) for each acceptor sequence;
   (v) selecting the acceptor sequence in the collection with the lowest preference score and the lowest backmutation score ("fr_bm");
   (vi) synthesizing a DNA segment encoding a humanized VL or VH sequence comprising CDRs from the donor immunoglobulin engrafted in the variable region framework from the selected acceptor sequence; and comprising key FR amino acids from the donor immunoglobulin that replace non-identical amino acids at corresponding amino acid positions in the acceptor variable region framework;
   (vii) introducing the DNA segment encoding the humanized VL or VH sequence and a DNA segment encoding a corresponding humanized VH or VL sequence into a cell; and
   (viii) expressing the DNA segments in the cell,
   wherein the lowest backmutation score is established by:
   (ix) providing a structural model of the donor immunoglobulin sequence;
   (x) identifying all key FR residues in the VL or VH sequence of the non-human donor immunoglobulin which are (a) within about 5 Angstroms of the CDRs of immunoglobulin and have a solvent exposure of less than 20% ("buried"); or (b) involved in the interaction with the CDR or another chain by specific hydrophobic, electrostatic or ion-ion chain interactions ("strltd"); and
   (xi) for each acceptor sequence in the collection, identifying the number of non-identical residues at the key FR positions of step (x) between the donor sequence and each acceptor sequence to establish a total backmutation score ("fr_bm") for each acceptor sequence;
   (xii) ranking the acceptor sequences in the collection based on the backmutation score;
   (xiii) identifying the acceptor sequence in the collection with the lowest backmutation score,
   thereby producing a humanized variant of a non-human donor immunoglobulin.

2. The method of claim 1, wherein the collection of all possible human immunoglobulin light chain variable region (VL) sequences is provided and the DNA segment encoding the humanized VL sequence is synthesized.

3. The method of claim 1, wherein the collection of all possible human immunoglobulin heavy chain variable region (VH) sequences is provided and the DNA segment encoding the humanized VH sequence is synthesized.

4. The method of claim 1, wherein the human VH or VL sequences are germline sequences.

5. The method of claim 1, wherein step (v) further comprises selecting the acceptor sequence in the collection with the lowest avoided backmutation ("avoid_bm") score, wherein lowest avoided backmutation scores is established by:
   (xiv) for each acceptor sequence in the collection, identifying the total number of non-identical FR residues from step (ii) and step (xi) that are listed in Table 1 to establish an avoided backmutation score;
   (xv) ranking the acceptor sequences in the collection based on the avoided backmutation score; and
   (xvi) identifying the acceptor sequence in the collection with the lowest avoided backmutation score.

6. The method claim 1, wherein step (ii) comprises identifying the number of non-identical residues at all framework region (FR) positions between Framework Regions 1-3 (FR1-3) of the donor sequence and FR1-3 of each acceptor sequence.

7. The method of claim 5, wherein the key CDR positions ("strcdr") are identified by:
   (xvii) providing a structural model of the non-human donor immunoglobulin sequence;
   (xviii) identifying all key FR residues in the VL or VH sequence of the non-human donor immunoglobulin which are involved in the interaction with the CDR or another chain by specific hydrophobic, electrostatic or ion-ion chain interactions ("strltd"); and (xix) identifying all CDR positions having CDR residues which interact with the key FR residues identified in step (xviii).

8. The method of claim 7, wherein the key FR amino acids from the donor immunoglobulin that replace the non-identical amino acids at corresponding FR positions in the selected acceptor variable region framework are identified by:

(xx) providing a structural model of the non-human donor immunoglobulin sequence;

(xxi) identifying all key FR residues (v1="strall"+ "strltd") in the VL or VH sequence of the non-human donor immunoglobulin which are (a) within about 5 Angstroms of the CDRs of the donor immunoglobulin sequence ("strall") or (b) involved in the interaction with the CDR or another chain by specific hydrophobic, electrostatic or ion-ion chain interactions ("strltd");

(xxii) comparing the key FR residues of step (xxi) with the residues present at corresponding amino acid positions in the selected acceptor variable region framework to identify all key FR residues that are non-identical.

9. The method of claim 7, wherein the key FR amino acids from the donor immunoglobulin that replace the non-identical amino acids at corresponding FR positions in the selected acceptor variable region framework are identified by:

(xx) providing a structural model of the non-human donor immunoglobulin sequence;

(xxi) identifying all key FR residues (v2="buried"+ "strltd") in the VL or VH sequence of the non-human donor immunoglobulin which are (a) within about 5 Angstroms of the CDRs of immunoglobulin and have a solvent exposure of less than 20% ("buried") or (b) involved in the interaction with the CDR or another chain by specific hydrophobic, electrostatic or ion-ion chain interactions ("strltd");

(xxii) comparing the key FR residues of step (xxi) with the residues present at corresponding amino acid positions in the selected acceptor variable region framework to identify all key FR residues that are non-identical.

10. The method of claim 7, wherein the key FR amino acids from the donor immunoglobulin that replace the non-identical amino acids at corresponding FR positions in the selected acceptor variable region framework are identified by:

(xx) providing a structural model of the non-human donor immunoglobulin sequence;

(xxi) identifying all key FR residues (v3="strltd") in the VL or VH sequence of the non-human donor immunoglobulin which are involved in the interaction with the CDR or another chain by specific hydrophobic, electrostatic or ion-ion chain interactions ("strltd");

(xxii) comparing the key FR residues of step (xxi) with the residues present at corresponding amino acid positions in the selected acceptor variable region framework to identify all key FR residues that are non-identical.

11. The method of claim 1, wherein said humanized variant has an on rate constant ($K_{on}$) to its target antigen that is substantially the same or greater than the non-human donor immunoglobulin.

12. The method of claim 1, wherein said DNA segment further comprising a linker polypeptide or an immunoglobulin constant domain.

13. The method of claim 12, wherein the constant domain comprises an amino acid sequence selected from the group consisting of SEQ ID Nos:10-13.

14. The method of claim 1, wherein said binding protein is selected from the group consisting of: an immunoglobulin molecule, a disulfide linked Fv, a monoclonal antibody, a scFv, a chimeric antibody, a single domain antibody, a CDR-grafted antibody, a diabody, a humanized antibody, a multispecific antibody, a Fab, a dual specific antibody, a Fab', a bispecific antibody; a F(ab')2, or a Fv.

* * * * *

SEQUENCE LISTING

<160> NUMBER OF SEQ ID NOS: 52

<210> SEQ ID NO 1
<211> LENGTH: 11
<212> TYPE: PRT
<213> ORGANISM: Homo sapiens

<400> SEQUENCE: 1

Trp Gly Gln Gly Thr Leu Val Thr Val Ser Ser
1               5                   10

<210> SEQ ID NO 2
<211> LENGTH: 11
<212> TYPE: PRT
<213> ORGANISM: Homo sapiens

<400> SEQUENCE: 2

Trp Gly Arg Gly Thr Leu Val Thr Val Ser Ser
1               5                   10

<210> SEQ ID NO 3
<211> LENGTH: 11
<212> TYPE: PRT
<213> ORGANISM: Homo sapiens

<400> SEQUENCE: 3

Trp Gly Gln Gly Thr Met Val Thr Val Ser Ser
1               5                   10

<210> SEQ ID NO 4
<211> LENGTH: 11
<212> TYPE: PRT
<213> ORGANISM: Homo sapiens

<400> SEQUENCE: 4

Trp Gly Gln Gly Thr Thr Val Thr Val Ser Ser
1               5                   10

<210> SEQ ID NO 5
<211> LENGTH: 10
<212> TYPE: PRT
<213> ORGANISM: Homo sapiens

<400> SEQUENCE: 5

Phe Gly Gln Gly Thr Lys Val Glu Ile Lys
1               5                   10

<210> SEQ ID NO 6
<211> LENGTH: 10
<212> TYPE: PRT
<213> ORGANISM: Homo sapiens

<400> SEQUENCE: 6

Phe Gly Gln Gly Thr Lys Leu Glu Ile Lys
1               5                   10

<210> SEQ ID NO 7
<211> LENGTH: 10
<212> TYPE: PRT
<213> ORGANISM: Homo sapiens

<400> SEQUENCE: 7

Phe Gly Pro Gly Thr Lys Val Asp Ile Lys
1               5                   10

<210> SEQ ID NO 8
<211> LENGTH: 10
<212> TYPE: PRT
<213> ORGANISM: Homo sapiens

<400> SEQUENCE: 8

```
Phe Gly Gly Gly Thr Lys Val Glu Ile Lys
1               5                   10
```

<210> SEQ ID NO 9
<211> LENGTH: 10
<212> TYPE: PRT
<213> ORGANISM: Homo sapiens

<400> SEQUENCE: 9

```
Phe Gly Gln Gly Thr Arg Leu Glu Ile Lys
1               5                   10
```

<210> SEQ ID NO 10
<211> LENGTH: 330
<212> TYPE: PRT
<213> ORGANISM: Homo sapiens

<400> SEQUENCE: 10

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 106
<212> TYPE: PRT
<213> ORGANISM: Homo sapiens

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 13
<211> LENGTH: 105
<212> TYPE: PRT
<213> ORGANISM: Homo sapiens

<400> SEQUENCE: 13

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 14
<211> LENGTH: 10
<212> TYPE: PRT
<213> ORGANISM: Homo sapiens

<400> SEQUENCE: 14

Phe Gly Thr Gly Thr Lys Val Thr Val Leu
1               5                   10

<210> SEQ ID NO 15
<211> LENGTH: 10
<212> TYPE: PRT
```

```
<213> ORGANISM: Homo sapiens

<400> SEQUENCE: 15

Phe Gly Gly Gly Thr Lys Leu Thr Val Leu
1               5                   10

<210> SEQ ID NO 16
<211> LENGTH: 10
<212> TYPE: PRT
<213> ORGANISM: Homo sapiens

<400> SEQUENCE: 16

Phe Gly Gly Gly Thr Gln Leu Thr Val Leu
1               5                   10

<210> SEQ ID NO 17
<211> LENGTH: 118
<212> TYPE: PRT
<213> ORGANISM: Unknown
<220> FEATURE:
<223> OTHER INFORMATION: Description of Unknown: Rodent antibody 10B3
      polypeptide

<400> SEQUENCE: 17

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Glu Met Val Trp Val Arg Gln Ala Pro Gly Glu Gly Leu Glu Trp Val
        35                  40                  45

Ala Tyr Ile Ser Ser Gly Ser Arg Thr Ile His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Ser Ser Leu Arg Ser Glu Asp Thr Ala Met Tyr Tyr Cys
                85                  90                  95

Ala Arg Thr Leu Leu Arg Leu His Phe Asp Tyr Trp Gly Gln Gly Thr
            100                 105                 110

Ile Leu Thr Val Ser Ser
        115

<210> SEQ ID NO 18
<211> LENGTH: 25
<212> TYPE: PRT
<213> ORGANISM: Unknown
<220> FEATURE:
<223> OTHER INFORMATION: Description of Unknown: Rodent antibody 10B3
      fr1 peptide

<400> SEQUENCE: 18

Glu Val Lys Leu Val Glu Ser Gly Gly Gly Leu Val Gln Pro Gly Gly
1               5                   10                  15

Ser Arg Lys Leu Ser Cys Ala Ala Ser
            20                  25

<210> SEQ ID NO 19
<211> LENGTH: 14
<212> TYPE: PRT
<213> ORGANISM: Unknown
<220> FEATURE:
<223> OTHER INFORMATION: Description of Unknown: Rodent antibody 10B3
      fr2 peptide
```

```
<400> SEQUENCE: 19

Trp Val Arg Gln Ala Pro Gly Glu Gly Leu Glu Trp Val Ala
1               5                   10

<210> SEQ ID NO 20
<211> LENGTH: 32
<212> TYPE: PRT
<213> ORGANISM: Unknown
<220> FEATURE:
<223> OTHER INFORMATION: Description of Unknown: Rodent antibody 10B3
      fr3 polypeptide

<400> SEQUENCE: 20

Arg Phe Thr Ile Ser Arg Asp Asn Pro Lys Asn Thr Leu Phe Leu Gln
1               5                   10                  15

Met Ser Ser Leu Arg Ser Glu Asp Thr Ala Met Tyr Tyr Cys Ala Arg
                20                  25                  30

<210> SEQ ID NO 21
<211> LENGTH: 11
<212> TYPE: PRT
<213> ORGANISM: Unknown
<220> FEATURE:
<223> OTHER INFORMATION: Description of Unknown: Rodent antibody 10B3
      fr4 peptide

<400> SEQUENCE: 21

Trp Gly Gln Gly Thr Ile Leu Thr Val Ser Ser
1               5                   10

<210> SEQ ID NO 22
<211> LENGTH: 10
<212> TYPE: PRT
<213> ORGANISM: Unknown
<220> FEATURE:
<223> OTHER INFORMATION: Description of Unknown: Rodent antibody 10B3
      cdr1 peptide

<400> SEQUENCE: 22

Gly Phe Thr Phe Ser Asp Tyr Glu Met Val
1               5                   10

<210> SEQ ID NO 23
<211> LENGTH: 17
<212> TYPE: PRT
<213> ORGANISM: Unknown
<220> FEATURE:
<223> OTHER INFORMATION: Description of Unknown: Rodent antibody 10B3
      cdr2 peptide

<400> SEQUENCE: 23

Tyr Ile Ser Ser Gly Ser Arg Thr Ile His Tyr Ala Asp Thr Val Lys
1               5                   10                  15

Gly

<210> SEQ ID NO 24
<211> LENGTH: 9
<212> TYPE: PRT
<213> ORGANISM: Unknown
<220> FEATURE:
<223> OTHER INFORMATION: Description of Unknown: Rodent antibody 10B3
      cdr3 peptide

<400> SEQUENCE: 24

Thr Leu Leu Arg Leu His Phe Asp Tyr
1               5
```

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Val Trp Val Arg Gln Ala Pro Gly Lys Gly Leu Glu Trp Val
        35                  40                  45

Ala Tyr Ile Ser Ser Gly Ser Arg Thr Ile His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Asn Ser Leu Arg Asp Glu Asp Thr Ala Val Tyr Tyr Cys
                85                  90                  95

Ala Arg Thr Leu Leu Arg Leu His Phe Asp Tyr Trp Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Val Trp Val Arg Gln Ala Pro Gly Lys Gly Leu Glu Trp Val
        35                  40                  45

Ala Tyr Ile Ser Ser Gly Ser Arg Thr Ile His Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Asn Ser Leu Arg Asp Glu Asp Thr Ala Val Tyr Tyr Cys
                85                  90                  95

Ala Arg Thr Leu Leu Arg Leu His Phe Asp Tyr Trp Gly Gln Gly Thr
            100                 105                 110

Leu Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Val Trp Val Arg Gln Ala Pro Gly Lys Gly Leu Glu Trp Val
        35                  40                  45

Ser Tyr Ile Ser Ser Gly Ser Arg Thr Ile His Tyr Ala Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Thr Leu Leu Arg Leu His Phe Asp Tyr Trp Gly Gln Gly Thr
            100                 105                 110

Leu Val Thr Val Ser Ser
            115
```

<210> SEQ ID NO 28
<211> LENGTH: 98
<212> TYPE: PRT
<213> ORGANISM: Unknown
<220> FEATURE:
<223> OTHER INFORMATION: Description of Unknown: Rodent antibody 10B3 polypeptide

<400> SEQUENCE: 28

```
Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Glu Met Val Trp Val Arg Gln Ala Pro Gly Glu Gly Leu Glu Trp Val
        35                  40                  45

Ala Tyr Ile Ser Ser Gly Ser Arg Thr Ile His Tyr Ala Asp Thr Val
50                  55                  60

Lys Gly Arg Phe Thr Ile Ser Arg Asp Asn Pro Lys Asn Thr Leu Phe
65                  70                  75                  80

Leu Gln Met Ser Ser Leu Arg Ser Glu Asp Thr Ala Met Tyr Tyr Cys
            85                  90                  95

Ala Arg
```

<210> SEQ ID NO 29
<211> LENGTH: 98
<212> TYPE: PRT
<213> ORGANISM: Homo sapiens

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Asp Glu Asp Thr Ala Val Tyr Tyr Cys
                    85                  90                  95

Ala Arg

<210> SEQ ID NO 30
<211> LENGTH: 98
<212> TYPE: PRT
<213> ORGANISM: Homo sapiens

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg

<210> SEQ ID NO 31
<211> LENGTH: 98
<212> TYPE: PRT
<213> ORGANISM: Homo sapiens

<400> SEQUENCE: 31

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg

<210> SEQ ID NO 32
<211> LENGTH: 98
<212> TYPE: PRT
<213> ORGANISM: Homo sapiens

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45
```

```
Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys

<210> SEQ ID NO 33
<211> LENGTH: 98
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Val Trp Val
            35                  40                  45

Ser Arg Ile Asn Ser Asp Gly Ser Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 34
<211> LENGTH: 98
<212> TYPE: PRT
<213> ORGANISM: Homo sapiens

<400> SEQUENCE: 34

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 35
<211> LENGTH: 98
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 36
<211> LENGTH: 98
<212> TYPE: PRT
<213> ORGANISM: Homo sapiens

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 37
<211> LENGTH: 98
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 38
<211> LENGTH: 98
<212> TYPE: PRT
<213> ORGANISM: Homo sapiens

```
<400> SEQUENCE: 38

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 39
<211> LENGTH: 98
<212> TYPE: PRT
<213> ORGANISM: Homo sapiens

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 40
<211> LENGTH: 98
<212> TYPE: PRT
<213> ORGANISM: Homo sapiens

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 41
<211> LENGTH: 98
<212> TYPE: PRT
<213> ORGANISM: Homo sapiens

<400> SEQUENCE: 41

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 42
<211> LENGTH: 98
<212> TYPE: PRT
<213> ORGANISM: Homo sapiens

<400> SEQUENCE: 42

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys

<210> SEQ ID NO 43
<211> LENGTH: 98
<212> TYPE: PRT
<213> ORGANISM: Homo sapiens

<400> SEQUENCE: 43

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys 85                  90                  95

Ala Arg

<210> SEQ ID NO 44
<211> LENGTH: 98
<212> TYPE: PRT
<213> ORGANISM: Homo sapiens

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 45
<211> LENGTH: 98
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 46
<211> LENGTH: 98
<212> TYPE: PRT
<213> ORGANISM: Homo sapiens

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 47
<211> LENGTH: 98
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ser Asn Ala Gly Asn Gly Asn Thr Lys Tyr Ser Gln Glu Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg

<210> SEQ ID NO 48
<211> LENGTH: 98
<212> TYPE: PRT
<213> ORGANISM: Homo sapiens

<400> SEQUENCE: 48

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
                20                  25                  30

Ala Met Gln Trp Val Arg Gln Ala Arg Gly Gln Arg Leu Glu Trp Ile
            35                  40                  45

Gly Trp Ile Val Val Gly Ser Gly Asn Thr Asn Tyr Ala Gln Lys Phe
        50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala

<210> SEQ ID NO 49
<211> LENGTH: 98
<212> TYPE: PRT
<213> ORGANISM: Homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30
```

-continued

Asp Ile Asn Trp Val Arg Gln Ala Thr Gly Gln Gly Leu Glu Trp Met
              35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 50
<211> LENGTH: 98
<212> TYPE: PRT
<213> ORGANISM: Homo sapiens

<400> SEQUENCE: 50

Gln Met Gln Leu Val Gln Ser Gly Pro Glu Val Lys Lys Pro Gly Thr
1               5                  10                  15

Ser Val Lys Val Ser Cys Lys Ala Ser Gly Phe Thr Phe Thr Ser Ser
                20                  25                  30

Ala Val Gln Trp Val Arg Gln Ala Arg Gly Gln Arg Leu Glu Trp Ile
              35                  40                  45

Gly Trp Ile Val Gly Ser Gly Asn Thr Asn Tyr Ala Gln Lys Phe
 50                  55                  60

Gln Glu Arg Val Thr Ile Thr Arg Asp Met Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ala

<210> SEQ ID NO 51
<211> LENGTH: 98
<212> TYPE: PRT
<213> ORGANISM: Homo sapiens

<400> SEQUENCE: 51

Gln Met Gln Leu Val Gln Ser Gly Ala Glu Val Lys Lys Thr Gly Ser
1               5                  10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
              35                  40                  45

Gly Trp Ile Thr Pro Phe Asn Gly Asn Thr Asn Tyr Ala Gln Lys Phe
 50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg

<210> SEQ ID NO 52
<211> LENGTH: 98
<212> TYPE: PRT
<213> ORGANISM: Homo sapiens

<400> SEQUENCE: 52

Gln Val Gln Leu Val Gln Ser Gly Ala Glu Val Lys Lys Pro Gly Ala

-continued

```
1               5                   10                  15
Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
            50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr
```